US010188485B2

United States Patent
Kim et al.

(10) Patent No.: US 10,188,485 B2
(45) Date of Patent: Jan. 29, 2019

(54) DENTAL APPLIANCE DETACHABLY ATTACHED TO THE TEETH, AND FABRICATING METHOD THEREFOR

(71) Applicant: UNIVERSITY-INDUSTRY COOPERATION GROUP OF KYUNG HEE UNIVERSITY, Yongin-si, Gyeonggi-do (KR)

(72) Inventors: Seong Hun Kim, Seoul (KR); Hyee-woong Kim, Seoul (KR)

(73) Assignee: UNIVERSITY-INDUSTRY COOPERATION GROUP OF KYUNG HEE UNIVERSITY, Yongin-si, Gyeonggi-do (KR)

( * ) Notice: Subject to any disclaimer, the term of this patent is extended or adjusted under 35 U.S.C. 154(b) by 0 days.

(21) Appl. No.: 14/909,982

(22) PCT Filed: Mar. 19, 2014

(86) PCT No.: PCT/KR2014/002297
§ 371 (c)(1),
(2) Date: Feb. 3, 2016

(87) PCT Pub. No.: WO2015/020293
PCT Pub. Date: Feb. 12, 2015

(65) Prior Publication Data
US 2016/0157962 A1 Jun. 9, 2016

(30) Foreign Application Priority Data

Aug. 9, 2013 (KR) .................. 10-2013-0094657
Sep. 25, 2013 (KR) .................. 10-2013-0113993
Nov. 5, 2013 (KR) .................. 10-2013-0133653

(51) Int. Cl.
*A61C 7/08* (2006.01)
*A61F 5/56* (2006.01)
(Continued)

(52) U.S. Cl.
CPC ............... *A61C 7/08* (2013.01); *A61F 5/566* (2013.01); *B29C 41/02* (2013.01); *B29C 65/48* (2013.01);
(Continued)

(58) Field of Classification Search
CPC ....... A61C 7/08; A61C 19/063; A63B 71/085; A61F 5/566; A61F 2005/563
See application file for complete search history.

(56) References Cited

U.S. PATENT DOCUMENTS 2,630,117 A * 3/1953 Coleman .............. A63B 71/085
128/861
3,527,219 A * 9/1970 Greenberg ........... A61C 19/063
128/861
(Continued)

FOREIGN PATENT DOCUMENTS

JP 04-092659 A 3/1992
JP WO 2009001565 A1 * 12/2008 ........... A63B 71/085
(Continued)

OTHER PUBLICATIONS

International Search Report in International Application No. PCT/KR2014/002297, dated Jun. 26, 2014.

*Primary Examiner* — Nicholas Lucchesi
*Assistant Examiner* — Shannel Wright
(74) *Attorney, Agent, or Firm* — Park, Kim & Suh, LLC

(57) ABSTRACT

Disclosed are a detachable dental appliance which is outstandingly durable and can protect the teeth from clenching and bruxism and a fabricating method therefor. The detachable dental appliance according to the present invention comprises: a cover frame in which a teeth recess is formed in the length direction and which consists of a laminar structure comprising a first cover layer of a hard material and a second cover layer of a soft material provided on the inside relative to the first cover layer; and a core frame of a hard (Continued)

material which is provided in the teeth recess of the cover frame and has a tooth-contacting surface shaped with impressions of end portions of a plurality of the teeth, and, here, the cover frame comprises: a cover inner wall constituting a wall on one side of the teeth recesses so as to be provided on the lingual side of the teeth; a cover outer wall constituting a wall on the other side of the teeth recesses so as to be provided along the front of the teeth; and a cover base linking the cover inner wall and the cover outer wall so as to close off the gap between a tooth and its opposing tooth. The detachable dental appliance according to the present invention absorbs shock due to clenching or grinding and so prevents damage to teeth, and is effective in maintaining tooth alignment and is outstandingly durable in sustained use.

10 Claims, 25 Drawing Sheets

(51) Int. Cl.
  *B29C 41/02* (2006.01)
  *B29C 65/48* (2006.01)
  *A61C 11/00* (2006.01)
  *B29K 23/00* (2006.01)
  *B29L 31/00* (2006.01)

(52) U.S. Cl.
  CPC ......... *A61C 11/00* (2013.01); *B29K 2023/083* (2013.01); *B29L 2031/753* (2013.01)

(56) References Cited

U.S. PATENT DOCUMENTS

| | | | | |
|---|---|---|---|---|
| 4,073,061 A * | 2/1978 | Bergersen | ................ | A61C 7/08 433/6 |
| 4,793,803 A * | 12/1988 | Martz | ................ | A61C 7/08 433/6 |
| 5,406,962 A * | 4/1995 | Adell | ................ | A61C 7/08 128/859 |
| 5,624,257 A * | 4/1997 | Farrell | ................ | A61C 7/08 128/861 |
| 6,343,932 B1 * | 2/2002 | Wiesel | ................ | A61C 5/00 433/215 |
| 6,986,354 B1 * | 1/2006 | Burns | ................ | A63B 71/085 128/859 |
| 8,459,987 B2 * | 6/2013 | Farrell | ................ | A61C 7/08 433/6 |
| 2001/0041320 A1 * | 11/2001 | Phan | ................ | A61C 7/00 433/6 |
| 2002/0142258 A1 * | 10/2002 | Chishti | ................ | A61C 7/00 433/6 |
| 2003/0205234 A1 * | 11/2003 | Bardach | ................ | A61C 19/063 128/861 |
| 2004/0103905 A1 * | 6/2004 | Farrell | ................ | A61C 7/08 128/861 |
| 2004/0154625 A1 * | 8/2004 | Foley | ................ | A63B 71/085 128/859 |
| 2004/0209218 A1 * | 10/2004 | Chishti | ................ | A61C 7/00 433/6 |
| 2009/0246724 A1 * | 10/2009 | Chen | ................ | A61C 7/08 433/6 |
| 2010/0129762 A1 * | 5/2010 | Mason | ................ | A61C 7/002 433/6 |
| 2010/0129763 A1 * | 5/2010 | Kuo | ................ | A61C 7/08 433/6 |
| 2010/0186756 A1 * | 7/2010 | Koizumi | ................ | A63B 71/085 128/861 |
| 2010/0261133 A1 * | 10/2010 | Lax | ................ | A61C 9/0006 433/71 |
| 2011/0005531 A1 * | 1/2011 | Manzo | ................ | A63B 71/085 128/862 |
| 2011/0030704 A1 * | 2/2011 | Hanna | ................ | A61C 7/08 128/861 |
| 2011/0174319 A1 * | 7/2011 | Busciglio | ................ | A61F 5/566 128/862 |
| 2012/0282565 A1 * | 11/2012 | Adell | ................ | A61C 7/08 433/6 |
| 2012/0312309 A1 * | 12/2012 | Zimmerman | ................ | A63B 71/085 128/861 |

FOREIGN PATENT DOCUMENTS

KR  10-0788763 B1  12/2007
WO  2009/001565 A1  12/2008

* cited by examiner

【FIG. 1】
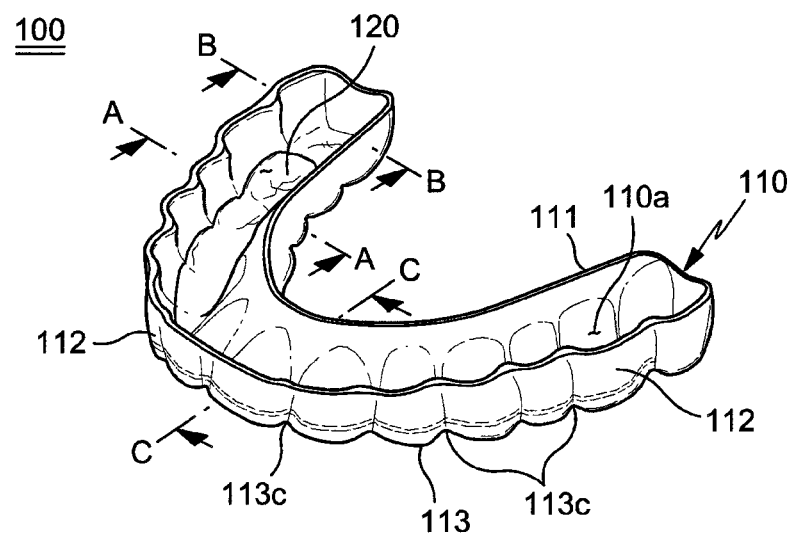
【FIG. 2】
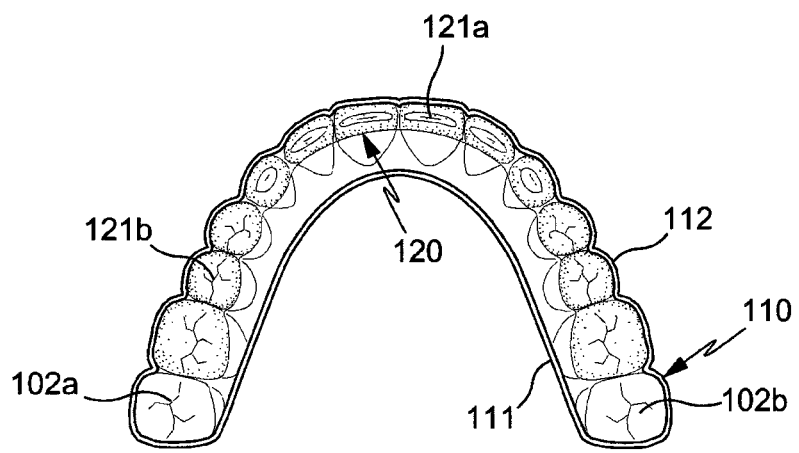

[FIG. 3]
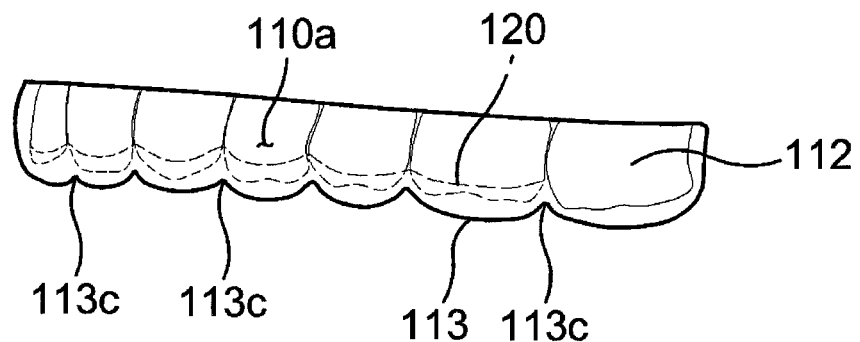
[FIG. 4]
120
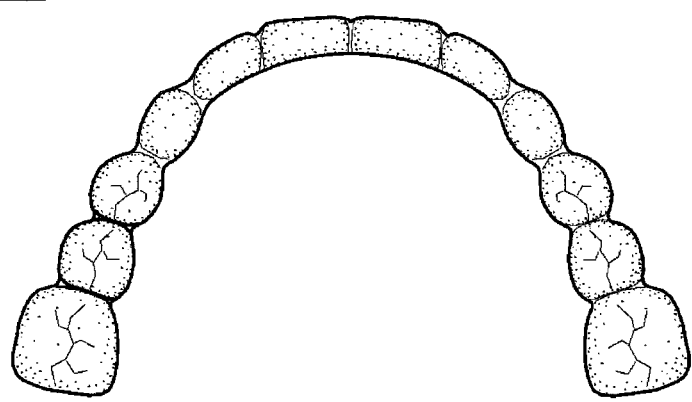

【FIG. 5】
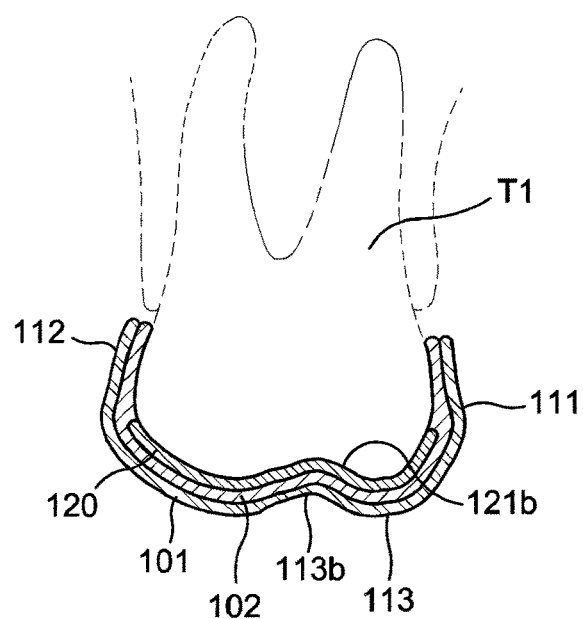
【FIG. 6】
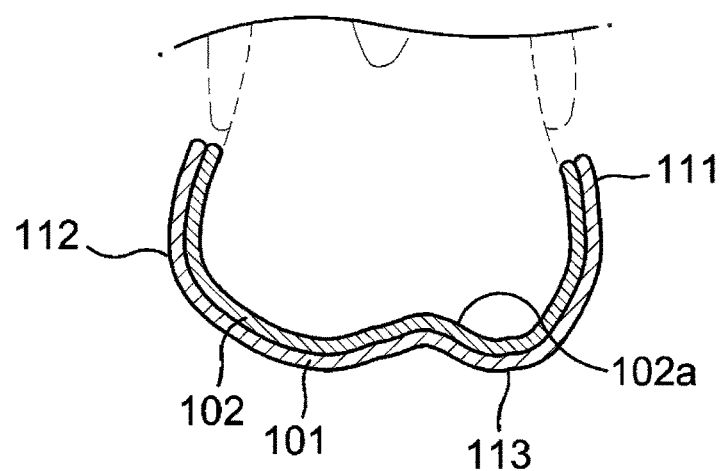

【FIG. 7】
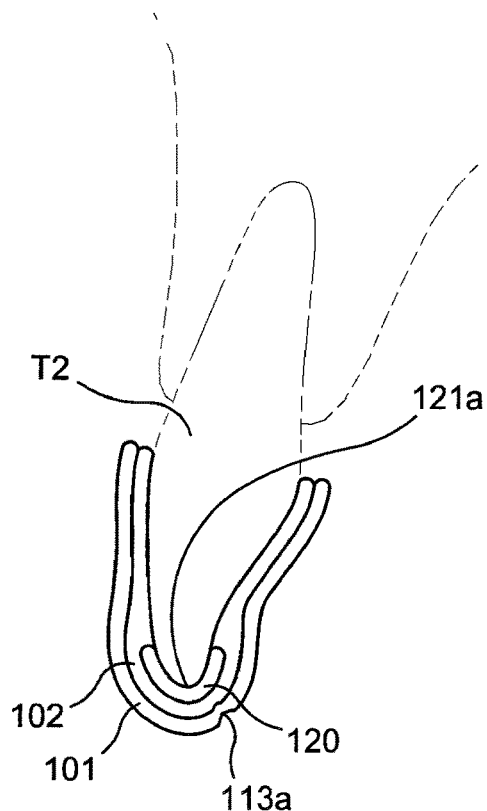
【FIG. 8】
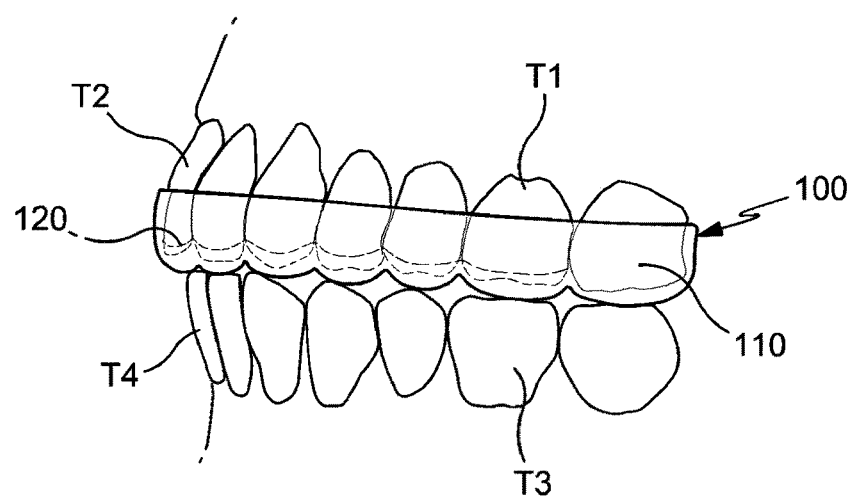

[FIG. 9]
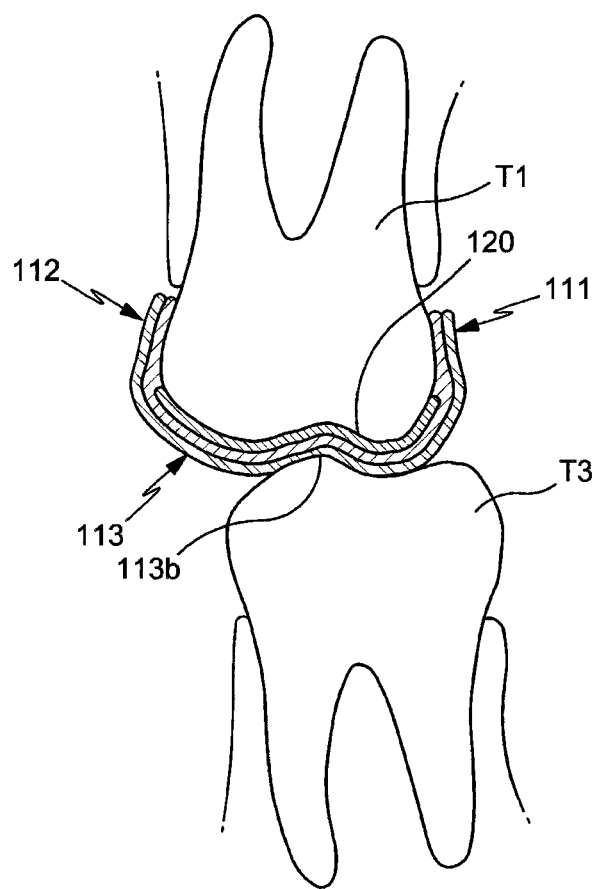

[FIG. 10]
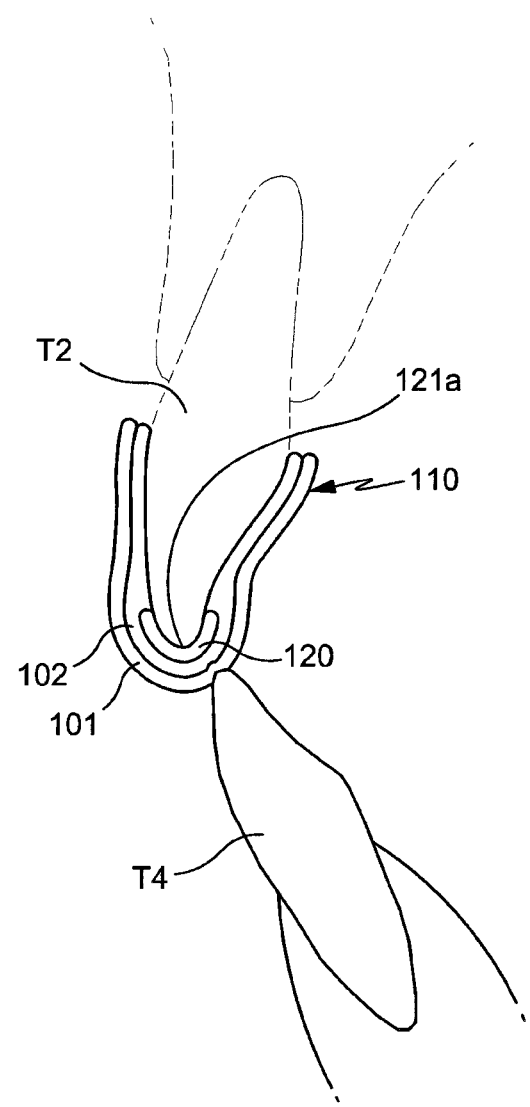

[FIG. 11]
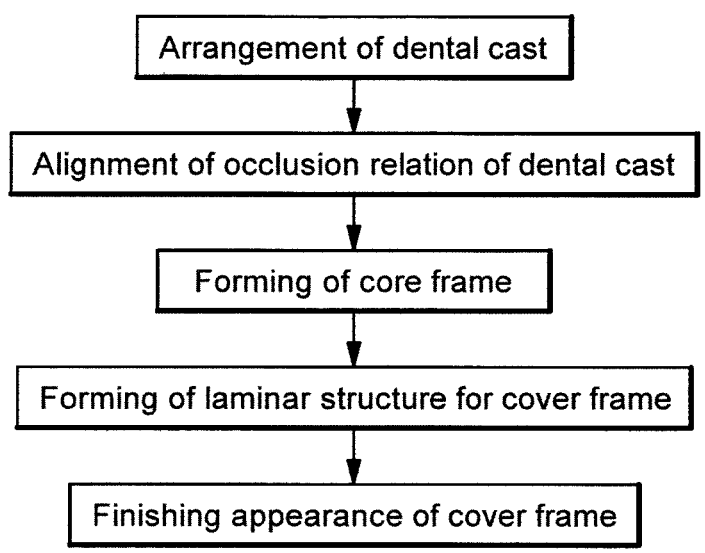

【FIG. 12】
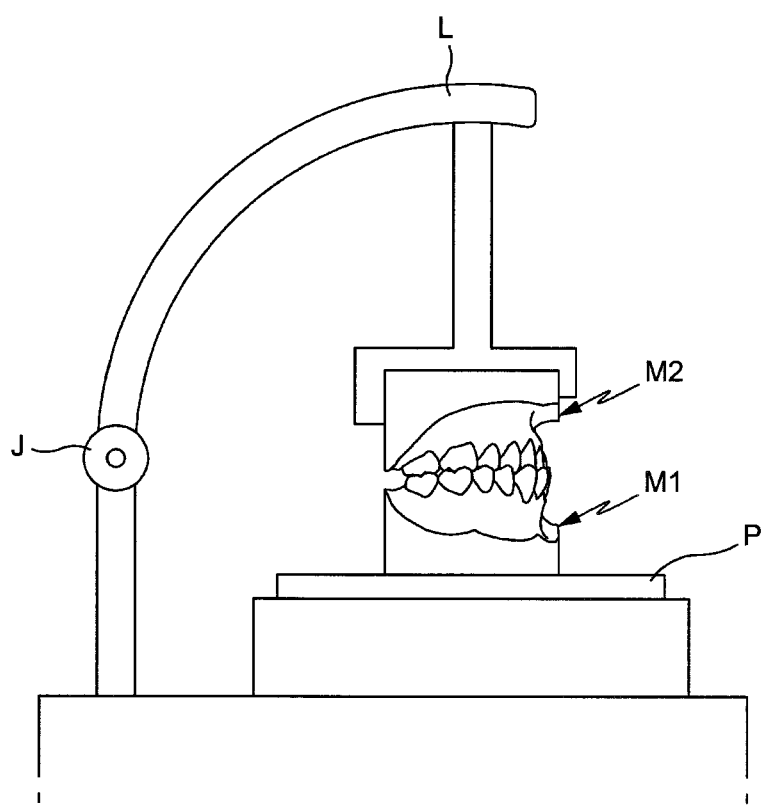

【FIG. 13】
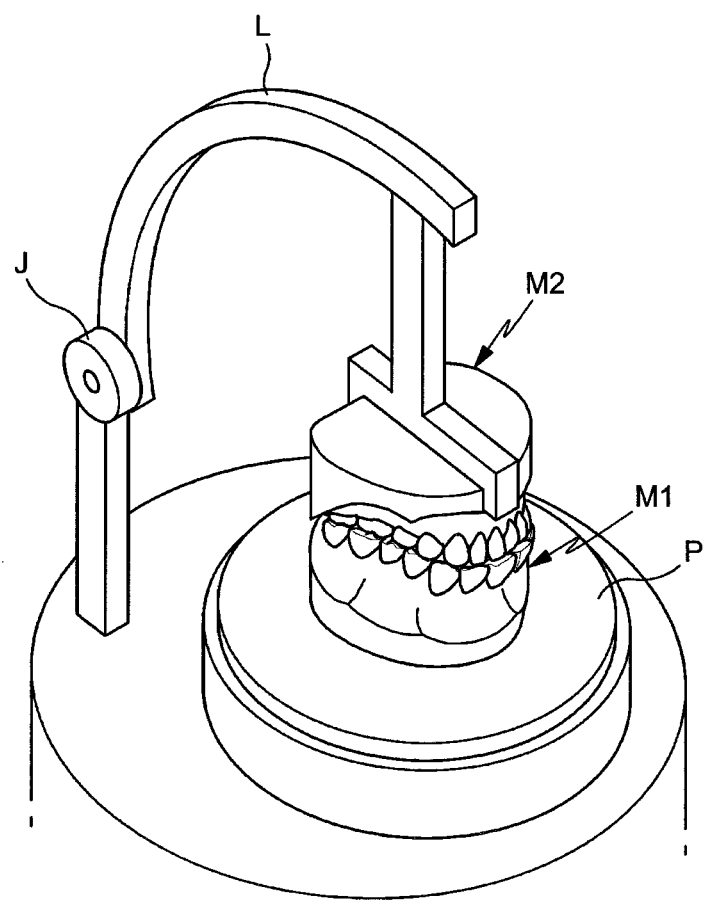

[FIG. 14]
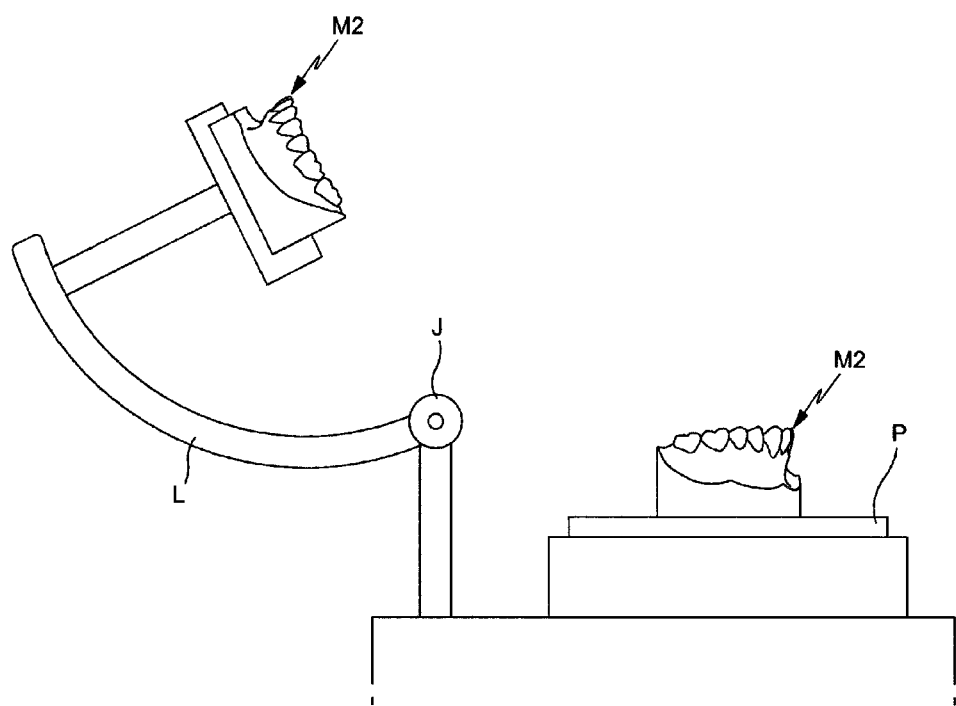

[FIG. 15]
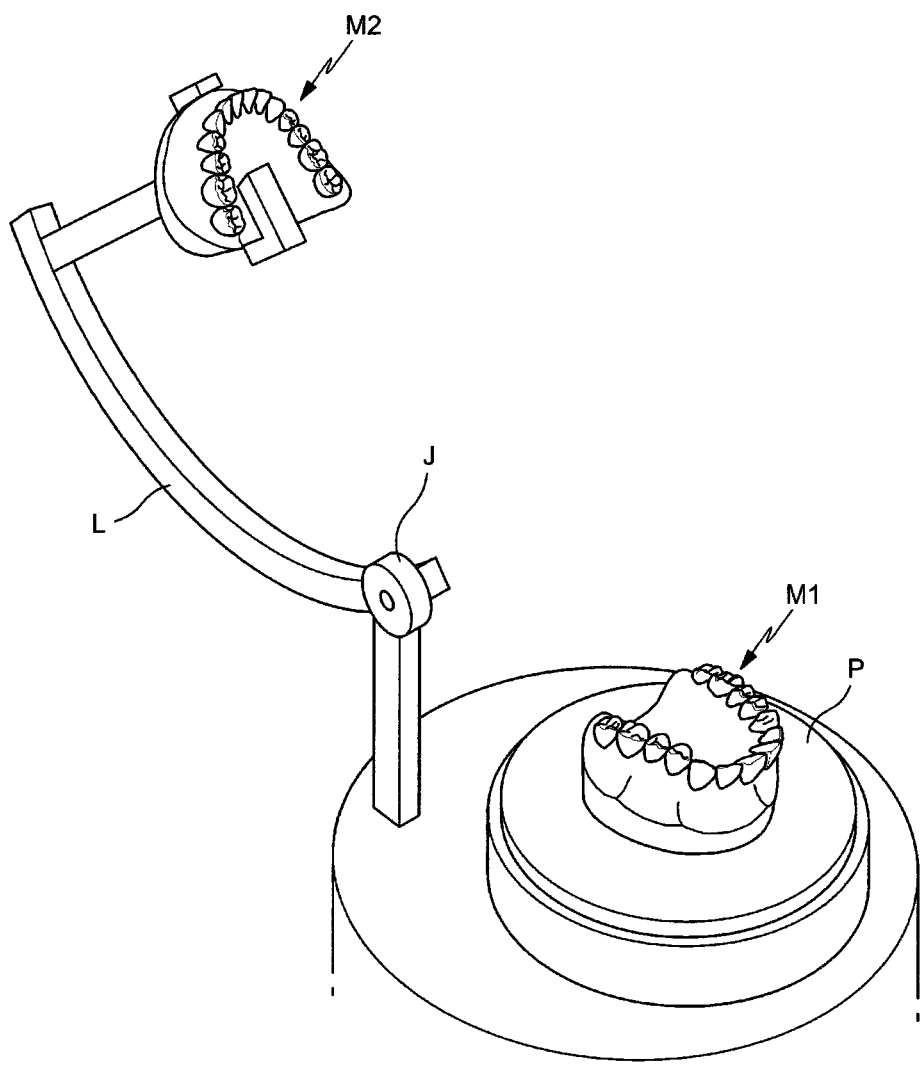

[FIG. 16]
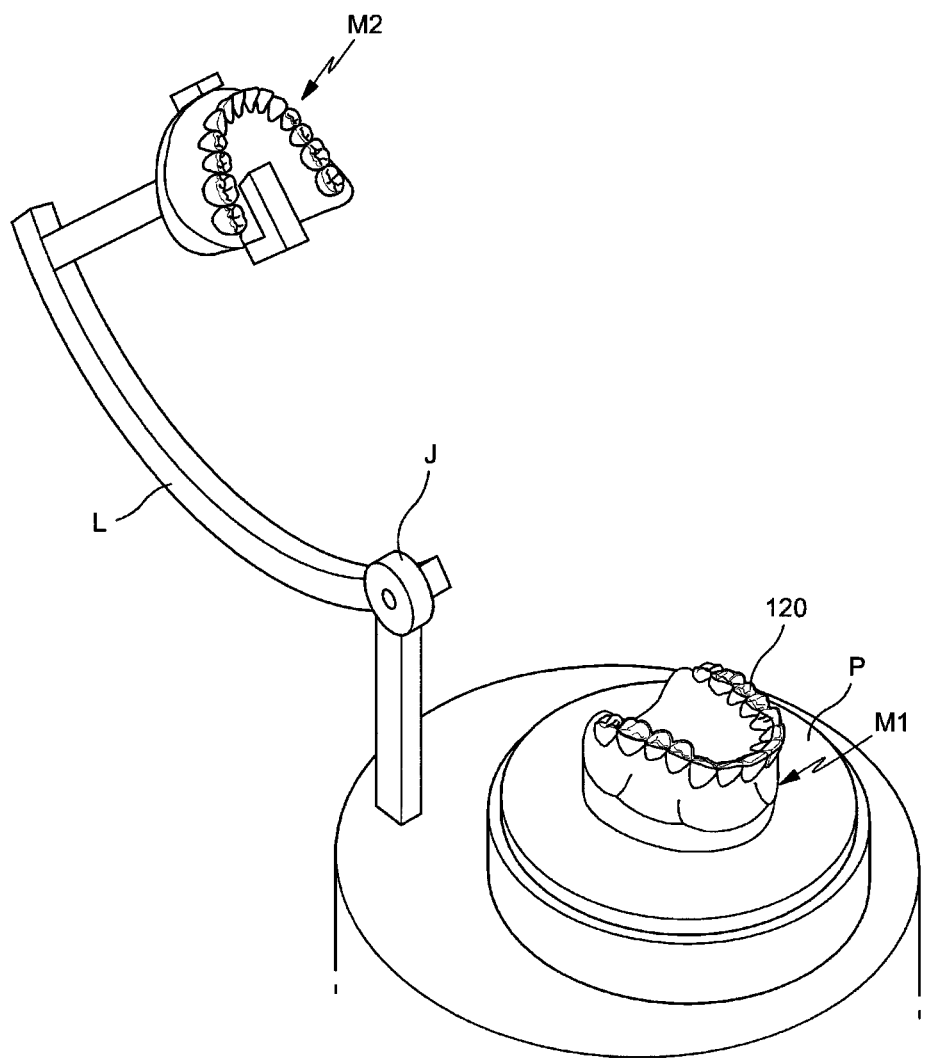

[FIG. 17]
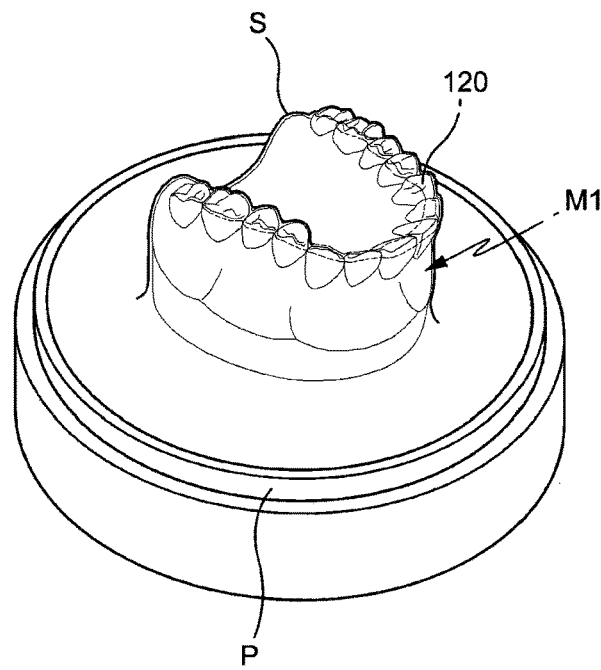
[FIG. 18]
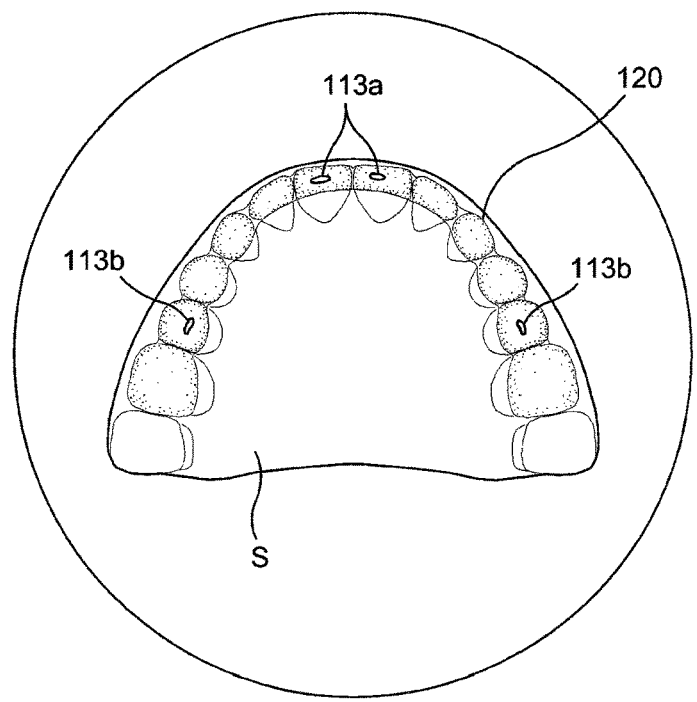

【FIG. 19】
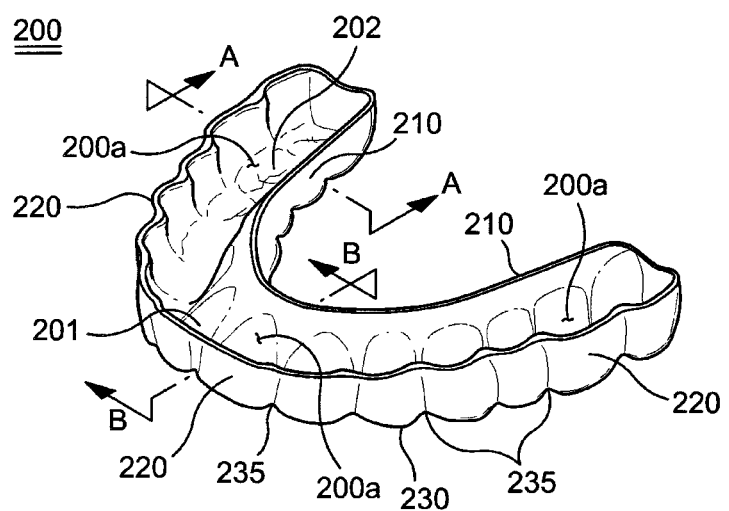
【FIG. 20】
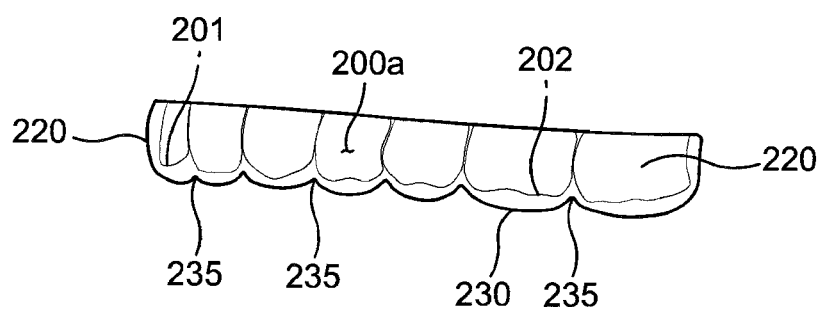

【FIG. 21】
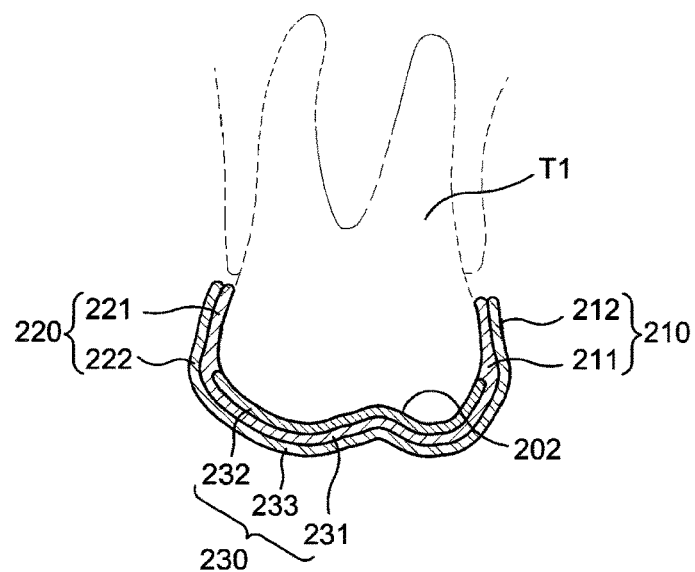
【FIG. 22】
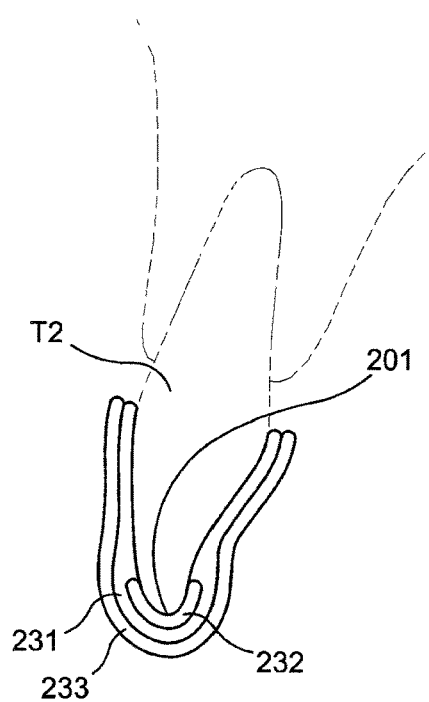

【FIG. 23】
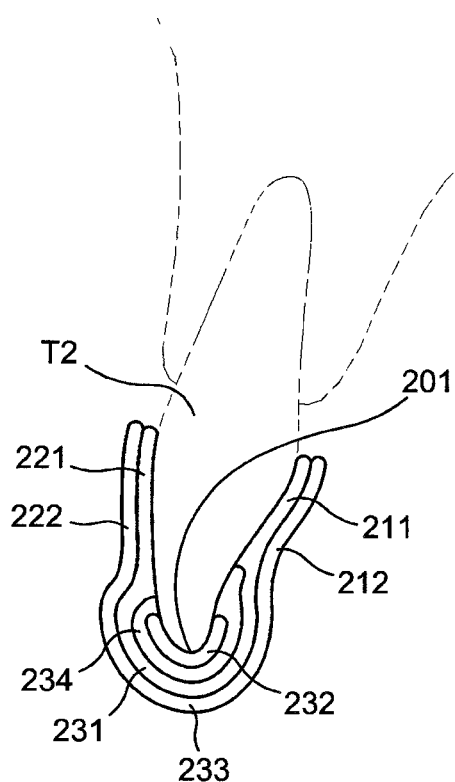
【FIG. 24】
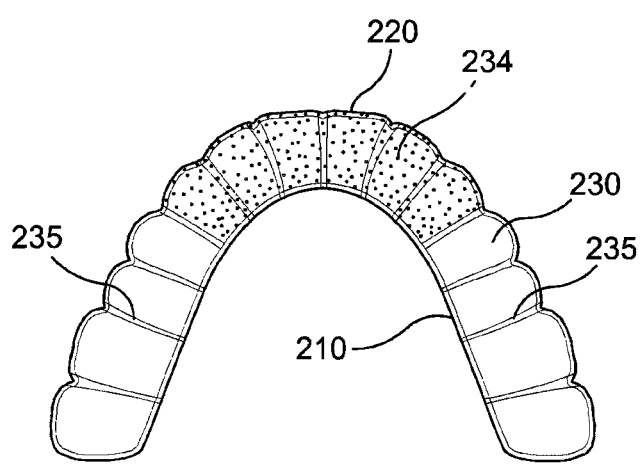

【FIG. 25】
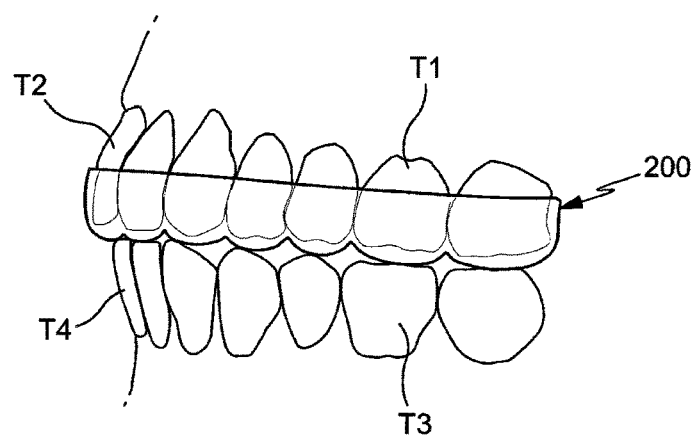
【FIG. 26】
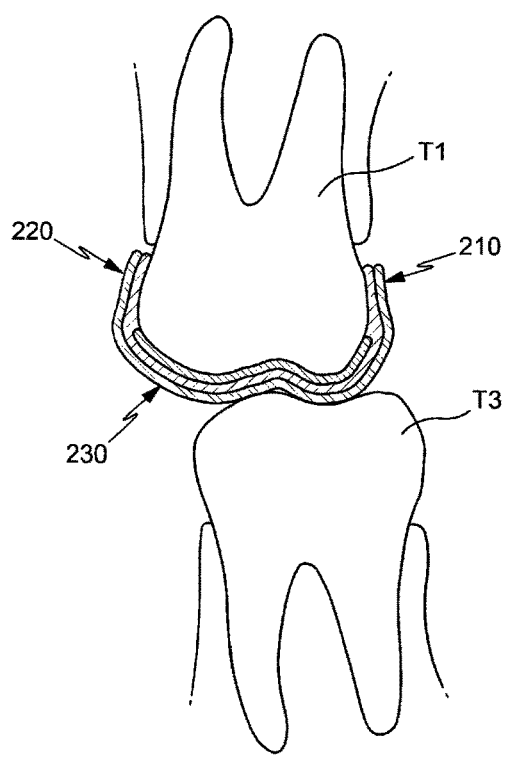

【FIG. 27】
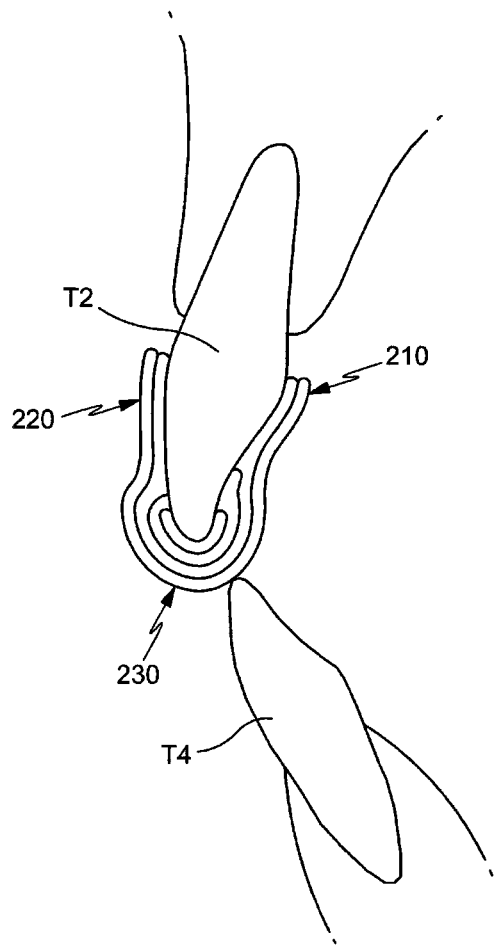

[FIG. 28]
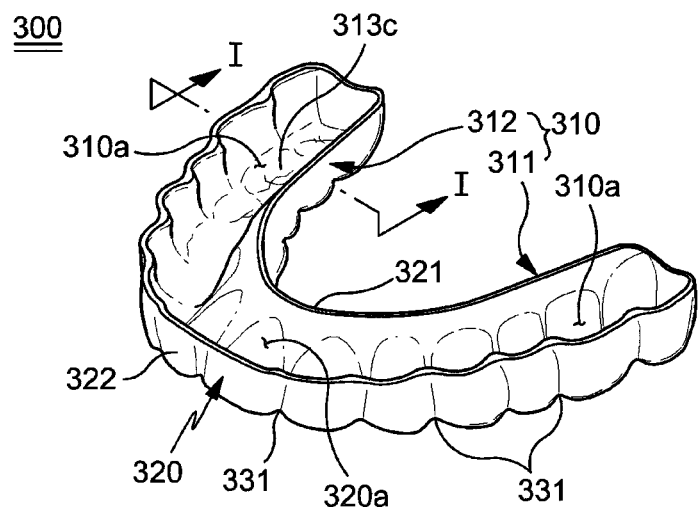
[FIG. 29]
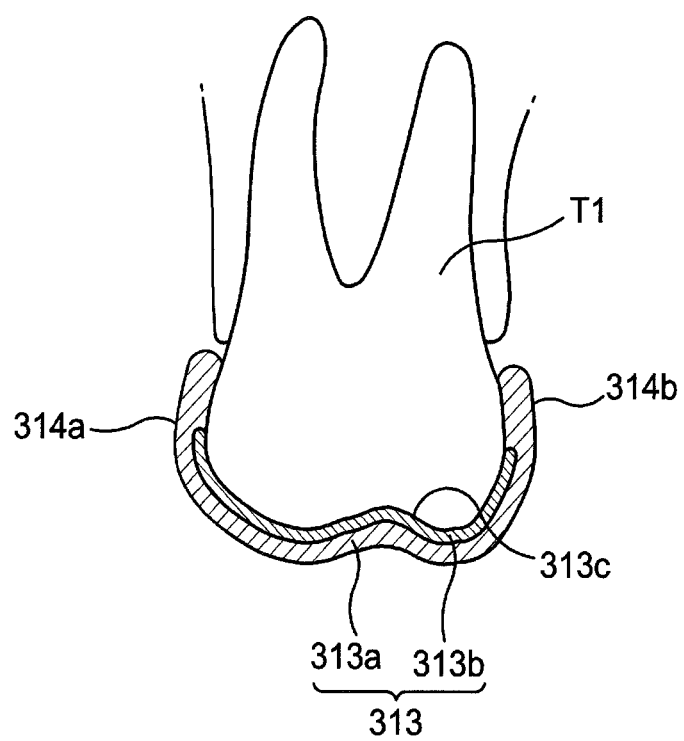

[FIG. 30]
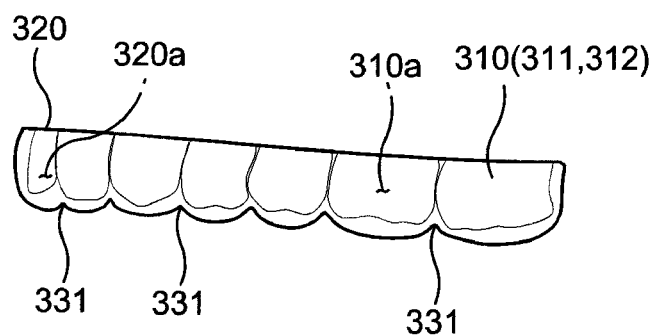
[FIG. 31]
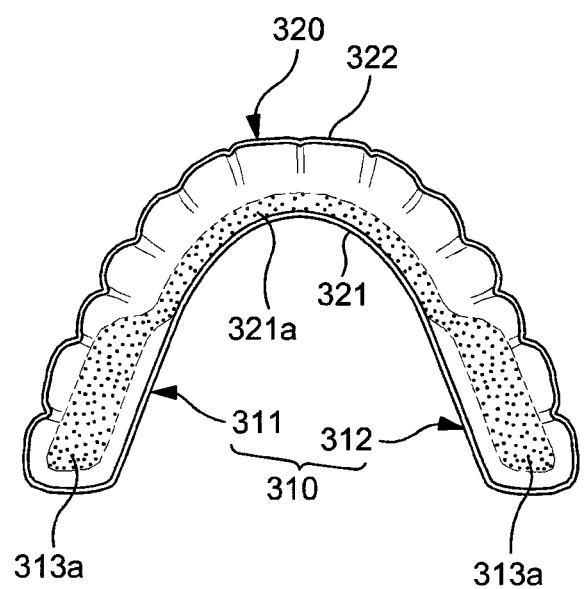

[FIG. 32]
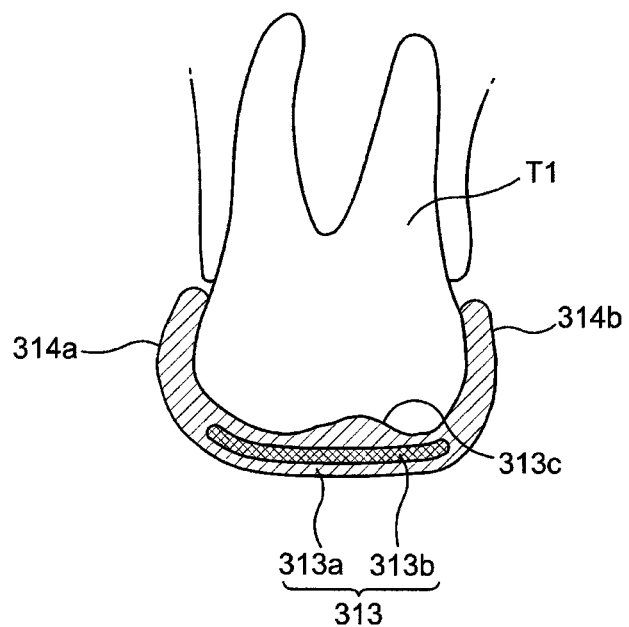
[FIG. 33]
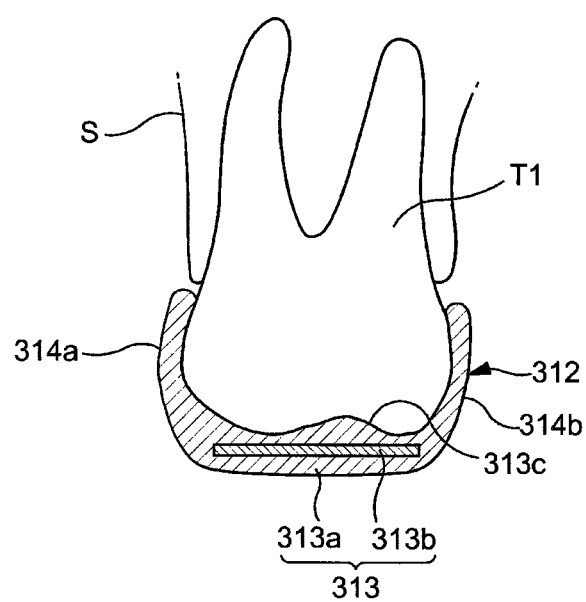

【FIG. 34】
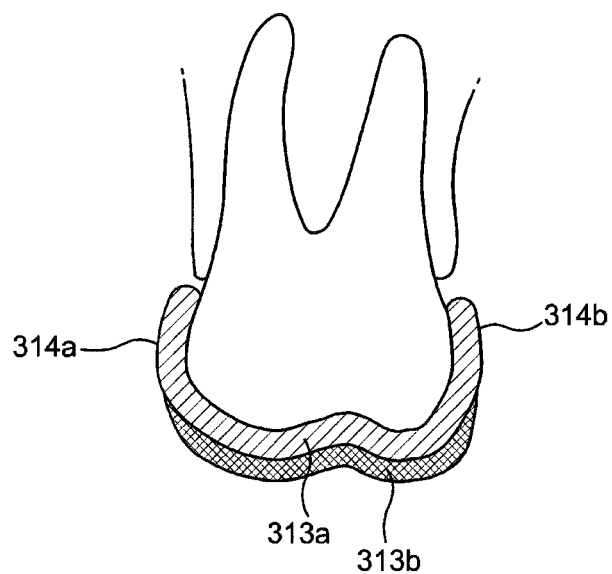
【FIG. 35】
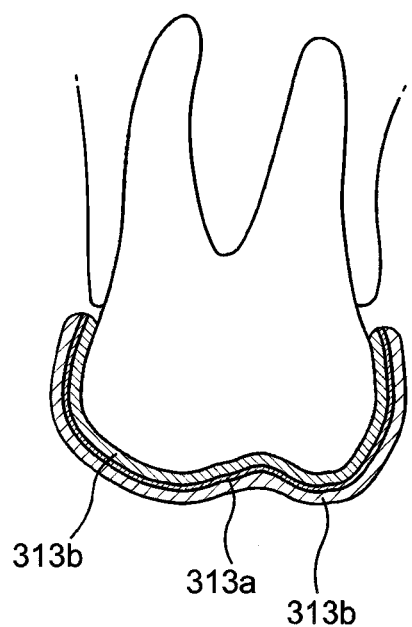

[FIG. 36]
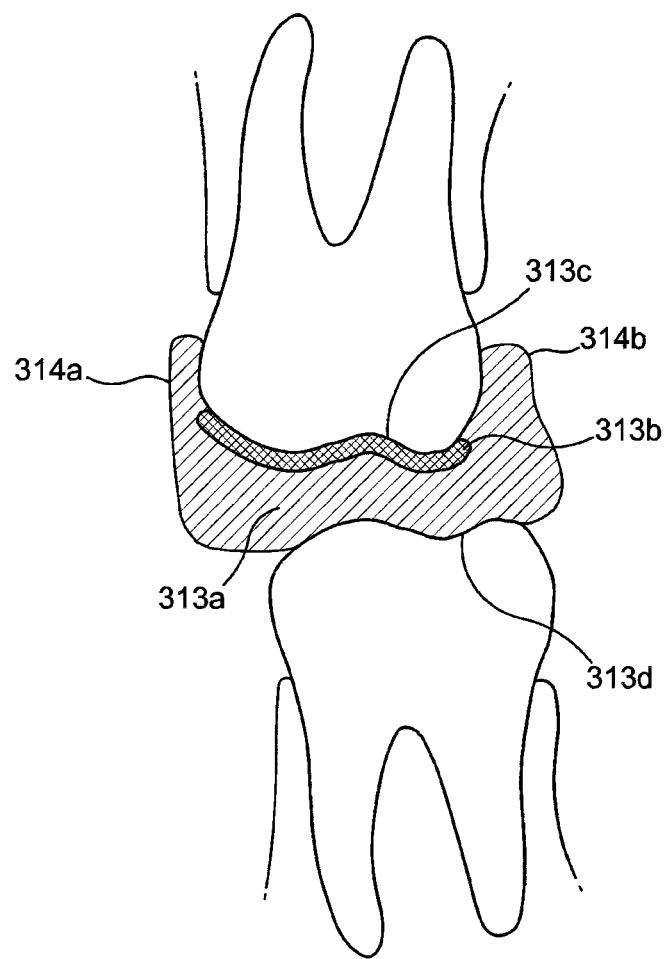

【FIG. 37】
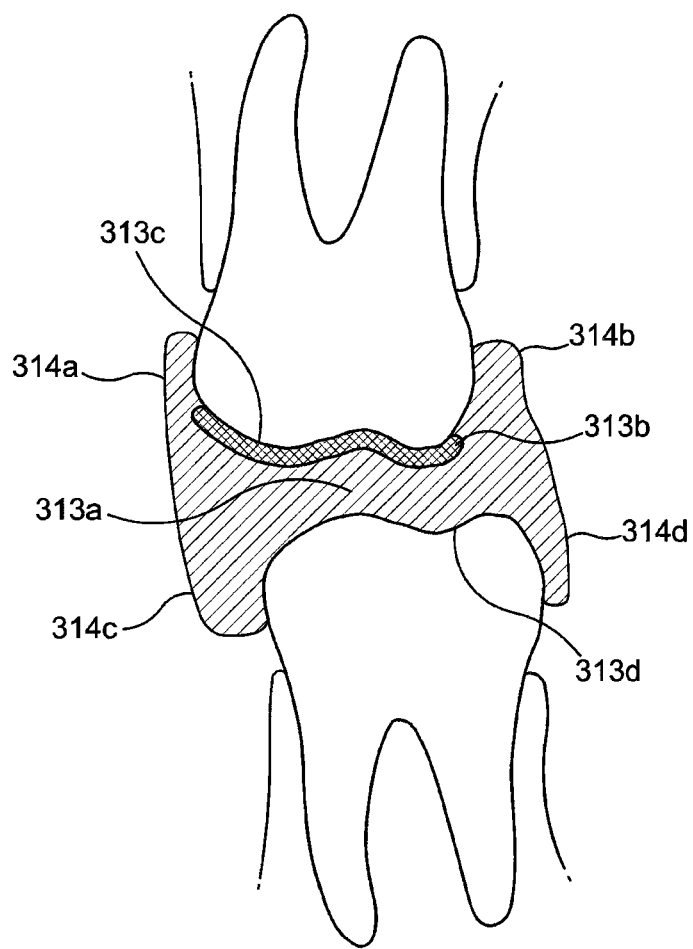

[FIG. 38]
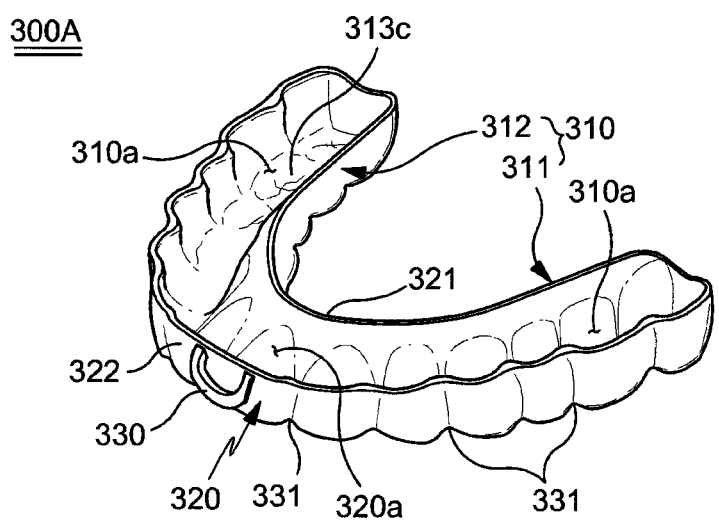
[FIG. 39]
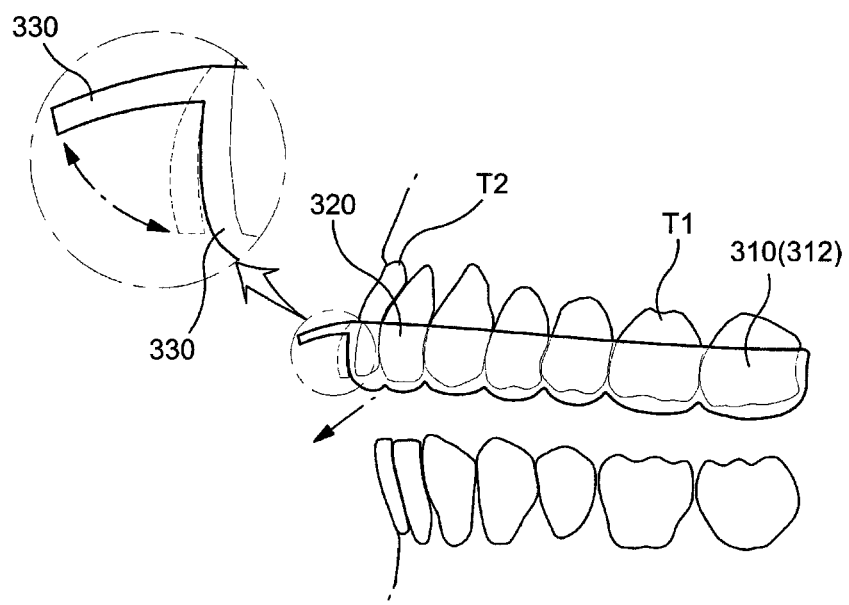

DENTAL APPLIANCE DETACHABLY ATTACHED TO THE TEETH, AND FABRICATING METHOD THEREFOR

CROSS-REFERENCE TO RELATED APPLICATIONS

This application is the National Stage filing under 35 U.S.C. 371 of International Application No. PCT/KR2014/002297, filed on Mar. 19, 2014, which claims the benefits of Korean Patent Application No. 10-2013-0094657, filed on Aug. 9, 2013, Korean Patent Application No. 10-2013-0113993, filed on Sep. 25, 2013, and Korean Patent Application No. 10-2013-0133653, filed on Nov. 5, 2013, the contents of which are all hereby incorporated by reference herein in their entirety.

TECHNICAL FIELD

The present invention relates to a detachable dental appliance to be attached to the teeth, and a fabricating method therefor, more specifically to a detachable dental appliance which is excellent in durability and wearing comfort, and furthermore can protect the teeth from a heavy occlusal force when clenching or grinding, can be easily produced and minimize or prevent a burden on the temporomandibular joint or teeth, and has an effective structure for maintaining tooth alignment, and a fabricating method therefor.

BACKGROUND ART

In general, detachable dental appliances refer to intraoral structures detachably mounted on the teeth to perform dental functions, for example, functions of protecting the teeth or temporomandibular joint, or maintaining tooth alignment after orthodontic treatment, etc. The detachable dental appliances include a mouth piece, a splint, an orthodontic retainer, an orthodontic aligner, etc. referred to as a transparent orthodontic aligner applying orthodontic force for tooth movement, which may be generally referred to as a mouth guard.

To be more specific, a mouth piece, one example of the detachable dental appliances, is mounted on the teeth to protect the teeth and temporomandibular joint from external shock applied to a face by a punch or a ball, etc. during workouts such as martial arts or ball games, etc., and is made of synthetic resin, rubber, silicone or latex, etc.

For reference, the human teeth form an arch-shaped alignment, that is, a dental arch, which is divided into normal occlusion and malocclusion depending on the location relation of tooth alignment in a state where the lower teeth and upper teeth are engaged with each other.

In the conventional art, general mouth pieces are provided for sports or leports, and are divided into ready-made mouth pieces and mouth pieces customized for individuals. Since the ready-made mouth pieces have reduced functionality, the customized mouth pieces produced in accordance with an individual's mouth structure (tooth alignment; dentition) is preferable. The mouth pieces are mounted on the teeth to prevent damage to teeth or gum, lip, etc. from shock applied from the outside of the face, protect the temporomandibular joint and jaw bone, and further prevent brain damage. Additionally, the orthodontic retainer is detachably attached to the teeth to maintain the tooth alignment.

Meanwhile, when a person is nervous or needs to exert a great strength, he/she may clench his/her teeth as muscle around the mouth becomes nervous. The temporomandibular joint and teeth absorb and disperse a heavy occlusal force (bite force) made at this time. However, when the occlusal force is excessively great or repeatedly occurs, this may give a bad influence on the teeth and temporomandibular joint.

Examples of cases where the teeth are damaged by the heavy occlusal force may be childbirth, workouts requiring a great strength, or physical labor, etc. During childbirth, a mother may clench her teeth due to birth pangs and clench her teeth when applying strain for smooth delivery. The occlusal force made at this time may damage the teeth of the mother and give a bad influence on the temporomandibular joint.

Additionally, the teeth are damaged due to repetition of unconscious grinding or clenching during sleep. As a conventional detachable dental appliance, the mouth piece is effective for protecting the teeth from the external shock applied to a face surface, but is insufficient to prevent damage to teeth due to the occlusion between the upper teeth and lower teeth such as clenching, grinding, etc. Also, there are many problems that the mouth piece is torn out by the heavy occlusal force, or the occlusal force by the clenching is not buffered, but is delivered to the teeth directly, the mouth piece is easily loosened after a predetermined period of use, thereby attenuating attaching property, and the mouth piece changes the tooth alignment between the lower teeth and upper teeth which results in a disorder in occlusion.

Furthermore, there is a problem that due to heavy fitting force, the tooth surface may be damaged when detaching the detachable dental appliance or pain may occur during the detachment. The conventional orthodontic retainer allows a direct contact between the upper teeth and lower teeth, so it is insufficient to protect the teeth from grinding or clenching. The above-mentioned problems also exist in detachable dental appliances in the form of a mouth piece, that is, an orthodontic retainer or a splint, etc.

DISCLOSURE

Technical Problem

The present invention was suggested to solve the above-mentioned problems. It is an object of the present invention to provide a detachable dental appliance which is capable of protecting the teeth from clenching or grinding and is excellent in durability, and a fabricating method therefor.

It is another object of the present invention to provide a detachable dental appliance such as a mouth guard, which is capable of minimizing or preventing a horizontal movement of the lower teeth for the upper teeth in use to protect the temporomandibular joint and is easily produced, and a fabricating method therefor.

It is yet another object of the present invention to provide a detachable dental appliance which allows smooth respiration even when clenching, and has a structure of minimizing modification, for example, loosening, due to a long period of use.

It is still another object of the present invention to provide a detachable dental appliance such as a mouth guard which absorbs a heavy occlusal force applied to an occlusal surface of a maxillary posterior teeth and a mandibular posterior teeth by an occlusion thereof to disperse/alleviate shock applied to the two posterior teeth, specifically to provide a mouth guard suitable for the mother.

It is yet still another object of the present invention to provide a detachable dental appliance such as a mouth guard, etc. with a structure preventing the dental arch of a user (a patient) from being in disorder during use of the appliance, that is, preventing the dental arch from being collapsed.

Specifically, the present invention provides a detachable dental appliance with a shape of mouth piece, for example, an intraoral apparatus such as a mouth guard or a splint, etc., and also provides a detachable dental appliance which can be used as an orthodontic retainer or an orthodontic aligner, etc.

Technical Solution

In order to achieve the above-mentioned objects, the present invention provides a detachable dental appliance with an arch shape detachably mounted on maxillary teeth (upper teeth) or mandibular teeth (lower teeth) forming a dental arch.

The detachable dental appliance according to the present invention includes a cover frame formed with a teeth recess in the longitudinal direction and which consists of a laminar structure including a first cover layer of a hard material and a second cover layer of a soft material provided on the inside relative to the first cover layer; and a core frame of a hard material which is provided in the teeth recess of the cover frame and has a tooth-contacting surface shaped with impressions of end portions of a plurality of the teeth, wherein the cover frame includes a cover inner wall constituting a wall on one side of the teeth recess so as to be provided on the lingual side of the teeth; a cover outer wall constituting a wall on the other side of the teeth recess so as to be provided along the front of the teeth; and a cover base connecting the cover inner wall and the cover outer wall so as to close off a gap between the teeth and their opposing teeth.

The tooth-contacting surface of the core frame is shaped with impressions of end portions of the teeth provided along the dental arch from any one of posterior teeth at left side to any one of posterior teeth at right side.

A left posterior teeth-contacting surface shaped with impressions of end portions of at least one of the posterior teeth at left side is formed between an end at left side of the teeth recess and an end at left side of the core frame so as to directly contact at least one of the posterior teeth at left side to be occluded; and a right posterior teeth-contacting surface shaped with impressions of end portions of at least one of the posterior teeth at right side is formed between an end at right side of the teeth recess and an end at right side of the core frame so as to directly contact at least one of the posterior teeth at right side to be occluded.

In the detachable dental appliance, it is preferable that a thickness of an anterior teeth cover part covering an end portion of the anterior teeth of the teeth is thicker than a thickness of a posterior teeth cover part covering an end of the farthest posterior teeth among the posterior teeth of the teeth.

Additionally, the first cover layer forms an outer surface of the detachable dental appliance, the second cover layer is laminated on the inner side of the first cover layer to contact the first cover layer, and an inner side surface of the second cover layer contacts the core frame to coat the core frame.

The cover inner wall contacts the lingual side surface of the teeth, and the cover outer wall contacts a front surface of the teeth, thereby maintaining a teeth attaching state of the detachable dental appliance.

More specifically, the second cover layer may contact the lingual side surface of the teeth, the front surface of the teeth, and the core frame.

The outer surface of the cover base may be shaped with an impression of opposing teeth of the teeth.

The cover base may have at least one airway groove dented on interdental portion of the outer surface of the cover base. The airway groove is formed in the direction crossing the longitudinal direction of the cover frame to allow air to pass through to the back of the cover frame.

As another embodiment, the present invention provides a method for producing a detachable dental appliance with an arch shape detachably mounted on the maxillary or mandibular teeth forming a dental arch.

The method for producing the detachable dental appliance according to the present invention includes the steps of (a) molding a core frame of a hard material which has a tooth-contacting surface shaped with impressions of end portions of a plurality of the teeth; and (b) forming a cover frame of a laminar structure including a first cover layer of a hard material and a second cover layer of a soft material provided on the inside relative to the first cover layer on the outside of the core frame, in order to integrally form a cover inner wall constituting a wall on one side of the teeth recess so as to be provided on the lingual side of the teeth; a cover outer wall constituting a wall on the other side of the teeth recess so as to be provided along the front of the teeth; and a cover base connecting the cover inner wall and the cover outer wall so as to close off the gap between the teeth and their opposing teeth, covering the core frame, and forming the teeth recess along with the cover inner wall and the cover outer wall, on the outside of the core frame.

The step (a) may be performed on a dental cast having the same structure as the teeth. The step (a) may include the step of (al) coating a dental resin on the dental cast for molding the tooth-contacting surface.

Additionally, the step (b) may include the step of forming a structure with a laminar structure for the cover frame on the outside of the core frame in a state where the core frame is arranged in the dental cast.

The step of forming the structure may include the steps of softening a sheet including a hard layer forming the first cover layer, and a soft layer forming the second cover layer, and laminated on the hard layer to be integrated with the hard layer; and adhering the sheet to the dental cast where the core frame is arranged so as to integrate the core frame with the sheet so that the shape of dental case where the core frame is arranged may be transcribed in intaglio on the sheet.

The step of forming the structure may include the steps of adhering the soft sheet to the dental cast where the core frame is arranged so as to integrate the core frame with the soft sheet so that the shape of dental case where the core frame is arranged may be transcribed in intaglio on the soft sheet forming the second cover layer; and adhering the hard sheet to the dental cast covered with the core frame and soft sheet so as to integrate the hard sheet with the outside of the soft sheet so that the shape of dental cast covered with the core frame and soft sheet may be transcribed in intaglio on the hard sheet forming the first cover layer.

The method for producing the detachable dental appliance may further include the step of forming an engagement recess shaped with an impression of the opposing teeth on the outer surface of the cover base by impressing a cast of the opposing teeth having the same structure as the opposing teeth of the teeth on the outer surface of the structure so as to correspond to the occlusion relation between maxilla and mandible.

Also, the method for producing the detachable dental appliance may further include the step of finishing the laminar structure to complete an appearance of the cover frame.

As another embodiment, the present invention provides a detachable dental appliance such as a teeth protector, etc. formed with a teeth recess into which the teeth are inserted, attached to the maxillary or mandibular teeth forming the dental arch so as to protect the teeth. The detachable dental appliance such as the teeth protector, etc. according to the embodiment of the present invention includes a guard inner wall constituting a wall on one side of the teeth recess so as to contact the lingual side surface of the teeth and covering the lingual side surface of the teeth; a guard outer wall constituting a wall on the other side of the teeth recess so as to contact the outer surface of the teeth and covering the outer surface of the teeth; and a guard base formed along the dental arch so as to cover a incisal surface of the anterior teeth constituting the end portion of the teeth and an occlusal surface of posterior teeth at both sides of the teeth, and connecting the guard inner wall and the guard outer wall so that the teeth may be inserted between the guard inner wall and the guard outer wall.

Additionally, the guard base includes a soft buffer layer which mitigates shock applied to the teeth; a hard inner base layer provided on the inside of the buffer layer with respect to the buffer layer; and a hard outer layer provided on the outside of the buffer layer with respect to the buffer layer.

The inner base layer includes a tooth-contacting surface shaped with impressions of end portions of the teeth inserted into the teeth protector, wherein the tooth-contacting surface includes an anterior teeth-contacting surface shaped with an impression of the incisal surface and a posterior teeth-contacting surface shaped with an impression of the occlusal surface.

The guard base contacts the anterior teeth of the opposing teeth opposing to the teeth and posterior teeth at both sides of the teeth. Additionally, a portion covering the anterior teeth of the teeth in the guard base is thicker than a portion covering the posterior teeth at both sides of the teeth.

The guard base may further include a thickness supplementing part provided on the inside of the outer base layer supplementing a thickness of the portion covering the anterior teeth of the teeth in the guard base.

The thickness supplementing part is provided on the outside of the inner base layer to be covered by the buffer layer, and the outer base layer forms the outer surface of the guard base.

The inner base layer is laminated while being adjacent to the inner surface of the buffer layer, and the outer base layer is laminated while being adjacent to the outer surface of the buffer layer to cover the buffer layer. Additionally, the outer base layer forms the outer surface of the guard base.

The outer base layer and inner base layer are made of a hard dental resin material, and the buffer layer is made of a soft dental resin material.

Additionally, each of the guard inner wall and the guard outer wall includes a soft first side surface layer and a hard second side surface layer provided on one side of the first side surface layer. The first side surface layer may be integrally formed with the buffer layer with the same material and is provided on the inside of the second side surface layer, and the second side surface layer may be integrally formed with the outer base layer with the same material.

The first side surface layer of the guard inner wall may be configured to contact the lingual side surface of the teeth, and the first side surface layer of the guard outer wall may be configured to contact the outer side surface of the teeth.

It is preferable that the guard base further includes an airway groove with a shape dented with the gap between the teeth at the outer surface of the teeth protector, which is formed in the direction crossing the dental arch of the teeth on the outer surface of the guard base to guide air flowing into the mouth.

As another embodiment, the present invention provides a detachable dental appliance such as a mouth piece, etc. attached to the maxillary teeth or mandibular teeth to protect the teeth and including a posterior teeth guard covering the posterior teeth of the teeth. The posterior teeth guard according to the embodiment of the present invention is configured to include a guard base covering the occlusal surface of the posterior teeth to cut off a gap between the occlusal surface of the posterior teeth and opposing teeth of the posterior teeth, and a guard side wall integrally formed with the guard base to cover the side surface of the posterior teeth, wherein the guard base includes a buffer layer absorbing shock by the occlusal force between the posterior teeth and opposing teeth, and a hard layer made of a firm material which reinforces a strength of the guard base.

The hard layer may be covered by the buffer layer to contact the occlusal surface of the posterior teeth. Additionally, the hard layer may have a posterior teeth-contacting surface with a shape where the occlusal surface of the posterior teeth is transcribed.

In contrast, the buffer layer may contact the occlusal surface of the posterior teeth, and have the posterior teeth-contacting surface with a shape where the occlusal surface of the posterior teeth is transcribed.

Additionally, the guard side wall includes posterior teeth buccal side wall adhered to a buccal side surface of the posterior teeth and a posterior teeth lingual side wall adhered to a lingual side surface of the posterior teeth, and prevents the posterior teeth guard from being separated from the posterior teeth.

The guard side wall includes a side surface layer integrally formed with the hard layer with the same material, and the guard base and guard side wall form a posterior teeth recess into which the posterior teeth is inserted, having a shape where the posterior teeth is transcribed. Of course, the guard side wall may include the side surface layer which is integrally formed with the buffer layer with the same material, and the guard base and guard side wall may form the posterior teeth recess with a shape where the posterior teeth is transcribed to be engaged therewith.

The detachable dental appliance such as a mouth piece, etc. according to the present invention may further include an airway groove with a shape dented with the gap between the teeth on the outer surface of the guard base, which is formed in the buccolingual direction on the outer surface of the guard base to guide air to the inside of the dental arch.

The posterior teeth guard is molar guard which is divided into a left guard for protecting the left molar teeth (posterior teeth at left side) and a right guard for protecting the right molar teeth (posterior teeth at right side), and the left guard and the right guard may be integrally linked by a connector.

The connector includes an anterior teeth guard formed with an anterior teeth recess with a shape where the anterior teeth is transcribed so that the anterior teeth of the teeth may be inserted. The left guard has a left posterior teeth recess with a shape where the posterior teeth at left side is transcribed so that the posterior teeth at left side of the posterior teeth may be inserted; and a right posterior teeth recess with a shape where the posterior teeth at right side is transcribed so that the posterior teeth at right side of the posterior teeth may be inserted. Additionally, the anterior teeth recess, the left posterior teeth recess and the right posterior teeth recess are formed to be the same as the dental arch of the teeth.

The anterior teeth guard may include a guard frame provided along at least any one side of the lingual side and labial side of the anterior teeth so as to maintain the shape of the dental arch.

The detachable dental appliance such as a mouth guard, etc. according to the embodiment of the present invention may include a handle for detaching a guard provided in the anterior teeth guard for detaching the mouth guard. The handle may be folded downwardly to the labial side wall of the anterior teeth guard contacting the labial side surface of the anterior teeth, but is not limited thereto.

The detachable dental appliance such as a mouth guard, etc. according to the embodiment of the present invention may be formed in the direction crossing the dental arch on the outer surface of the mouth guard to guide air to the inside of the dental arch, and may form the airway groove with a shape dented with the gap between the teeth on the outer surface of the mouth guard, that is, the outer surface of the detachable dental appliance.

An opposing teeth-contacting surface with a shape where the occlusal surface of the opposing teeth is transcribed may be formed on the outer surface of the guard base contacting the opposing teeth.

Advantageous Effects

According to the detachable dental appliance such as the mouth guard, etc. and a fabricating method therefor suggested in the present invention, the following effects may be exhibited.

First, the detachable dental appliance according to the present invention absorbs the shock due to clenching or grinding to prevent damage to teeth, is effective in maintaining tooth alignment, and is outstandingly durable in sustained use.

Secondly, since the detachable dental appliance according to the present invention may provide a fitting force suitable for the detachment thereof, it may prevent damage to teeth during detachment, may be easily detached, and has excellent resistance and shape stability for long period of use or shock.

Thirdly, the detachable dental appliance according to the present invention may secure smooth respiration even when clenching the teeth unconsciously or clenching the teeth consciously for exerting great power. Additionally, since an anterior teeth cover part covering the end portion of the anterior teeth is thicker than a posterior teeth cover part covering the farthest posterior teeth in the posterior teeth, this may prevent the change in vertical position of the teeth during the use of the detachable dental appliance.

Fourthly, according to the present invention, the detachable dental appliance may maintain the occlusion relation between the upper teeth and the lower teeth as it is, prevent or minimize the damage of the temporomandibular joint according to the horizontal movement of the lower teeth for the upper teeth, and be easily produced.

Fifthly, according to the present invention, since the buffer layer and hard layer cover the posterior teeth, the shock due to the heavy occlusal force may be absorbed and the damage may be prevented at the same time. Additionally, stable clenching may be induced and thereby the teeth and temporomandibular joint may be protected, and the present invention is very effective for a user in a situation requiring a heavy clenching, for example, a mother during childbirth.

Sixthly, according to the present invention, since the dental arch of the user may be maintained, damage to the teeth due to the disorder of the dental arch (collapse of the dental arch), damage to the alveolar bone, and damage to the temporomandibular joint may be prevented, and damage to the teeth due to the grinding may be prevented.

Seventhly, the detachable dental appliance such as a mouth guard, etc. according to the embodiment of the present invention may be easily detached, is convenient for use, and furthermore, may minimize the feeling of irritation.

DESCRIPTION OF THE DRAWINGS

FIG. 1 is a perspective view schematically illustrating one embodiment of a detachable dental appliance according to the present invention;

FIG. 2 is a plan view schematically illustrating one embodiment of the detachable dental appliance according to the present invention;

FIG. 3 is a side view schematically illustrating one embodiment of the detachable dental appliance according to the present invention;

FIG. 4 is a bottom view schematically illustrating one embodiment of a core frame applied to the detachable dental appliance according to the present invention;

FIG. 5 is a cross-sectional view taken along line A-A of FIG. 1;

FIG. 6 is a cross-sectional view taken along line B-B of FIG. 1;

FIG. 7 is a cross-sectional view taken along line C-C of FIG. 1;

FIG. 8 is a side view illustrating the contact state of one embodiment of the detachable dental appliance and the opposing teeth according to the present invention;

FIG. 9 is a cross-sectional view illustrating a state where posterior teeth of the opposing teeth contact the detachable dental appliance illustrated in FIG. 5;

FIG. 10 is a cross-sectional view illustrating a state where anterior teeth of the opposing teeth contact the detachable dental appliance illustrated in FIG. 7;

FIG. 11 is a flow chart exemplifying a method for producing the detachable dental appliance according to the present invention;

FIGS. 12 and 13 are a side view and a perspective view exemplifying a state where maxillary and mandibular dental casts are supported in a joint linkage device with an occlusion relation being aligned;

FIGS. 14 and 15 are a side view and a perspective view exemplifying a state where the maxillary and mandibular dental casts are widened by a joint linkage device with the occlusion relation being aligned;

FIG. 16 is a perspective view illustrating a state where a core frame is molded in the dental cast;

FIG. 17 is a perspective view illustrating a state where a laminar structure for a cover frame is covered on the core frame arranged in the dental cast;

FIG. 18 is a plan view illustrating a state where an engagement recess is formed on a surface of the laminar structure molded in FIG. 17;

FIG. 19 is a perspective view illustrating another embodiment of the present invention;

FIG. 20 is a side view illustrating another embodiment of the present invention;

FIG. 21 is a cross-sectional view taken along line A-A of FIG. 19;

FIG. 22 is a cross-sectional view taken along line B-B of FIG. 19;

FIG. 23 is another example of the cross-sectional view taken along line B-B of FIG. 19;

FIG. 24 is a bottom view illustrating yet another embodiment of the present invention;

FIG. 25 is a side view illustrating a state where the embodiment illustrated in FIG. 20 is mounted on the teeth;

FIG. 26 is a cross-sectional view illustrating a state where the posterior teeth of the opposing teeth contacts a portion illustrated in FIG. 21;

FIG. 27 is a cross-sectional view illustrating a state where the anterior teeth of the opposing teeth contacts a portion illustrated in FIG. 23;

FIG. 28 is a perspective view illustrating yet another embodiment of the present invention;

FIG. 29 is a cross-sectional view taken along line I-I of FIG. 28;

FIG. 30 is a side view of the embodiment illustrated in FIG. 28;

FIG. 31 is a plan view of the embodiment illustrated in FIG. 28;

FIGS. 32 to 37 are cross-sectional views illustrating yet other embodiments of the present invention;

FIG. 38 is a perspective view illustrating yet another embodiment of the present invention; and FIG. 39 is a side view illustrating a state where the embodiment illustrated in FIG. 38 is attached to the teeth.

BEST MODE

Hereinafter, preferred embodiments of the present invention to achieve the above-described objects will be described with reference to the accompanying drawings. In the following description of the embodiments, the same terms or characters will be used to refer to the same elements, and additional or redundant explanations thereon will be omitted below.

First, one embodiment of a detachable dental appliance according to the present invention is explained with reference to FIGS. 1 to 7.

FIG. 1 is a perspective view schematically illustrating one embodiment of a detachable dental appliance according to the present invention, FIG. 2 is a plan view schematically illustrating one embodiment of the detachable dental appliance according to the present invention, FIG. 3 is a side view schematically illustrating one embodiment of the detachable dental appliance according to the present invention, and FIG. 4 is a bottom view schematically illustrating one embodiment of a core frame applied to the detachable dental appliance according to the present invention.

Additionally, FIG. 5 is a cross-sectional view taken along line A-A of FIG. 1, FIG. 6 is a cross-sectional view taken along line B-B of FIG. 1, and FIG. 7 is a cross-sectional view taken along line C-C of FIG. 1.

The detachable dental appliance according to an embodiment of the present invention is an intraoral apparatus with a shape of a mouth piece and is detachably attached to the maxillary teeth (upper teeth) or mandibular teeth (lower teeth) forming a dental arch, that is, the upper teeth or the lower teeth to be applicable for dental functions such as protecting the teeth from external shock and environment such as grinding, clenching, etc. or maintaining tooth alignment. The detachable dental appliance may be used as a mouth piece, a splint or orthodontic retainer, etc. In the present embodiment, a structure where the detachable dental appliance is attached to the maxillary teeth (upper teeth) is explained, but it may also have a structure attached to the mandibular teeth (lower teeth). In case of being attached to the lower teeth, a teeth binding recess may be formed in the opposite direction.

Referring to FIGS. 1 to 7, in one embodiment according to the present invention, the dental appliance 100 may be detachably attached to the maxillary teeth (upper teeth) of a user. As stated above, the dental appliance 100 may be used as an apparatus for preventing damage to the teeth from grinding, clenching, and other shock, and also may be used as an apparatus for maintaining the current set of teeth (dentition), for example, an orthodontic retainer maintaining the tooth alignment after orthodontic treatment.

In the detachable dental appliance 100, the teeth binding recess 110a into which the teeth, that is, the upper teeth are inserted is formed in intaglio with a shape corresponding to the maxillary teeth forming a dental arch. Additionally, the detachable dental appliance 100 is an arch-shaped structure including a cover frame 110 and a core frame 120.

The cover frame 110 is a laminar structure with a plurality of laminar structures, more specifically is a laminar structure having a first cover layer 101 of a hard material and a second cover layer 102 of a soft material provided in the inside of the first cover layer 101. The second cover layer 102 may directly contact the inner side surface of the first cover layer 101 and may be laminated with another layer therebetween. However, in the present embodiment, the second cover layer is laminated while being adjacent to the inner side surface of the first cover layer 101.

Additionally, since the detachable dental appliance 100 according to the present embodiment is a structure attached to the upper teeth, a teeth recess is formed along the longitudinal direction of the cover frame 110 so as to accommodate the teeth, that is, the upper teeth, on the inside the cover frame 110. The cover frame 110 forms the appearance of the detachable dental appliance 100 according to the present embodiment to have an arch shape, and is provided in a downwardly dented shape at the top of the cover frame 110 so that the teeth recess may correspond to the dental arch.

More specifically, the cover frame 110 includes a cover inner wall 111, a cover outer wall 112 and a cover base 113. Here, the cover inner wall 111 forms one side wall (inner side wall or back wall) of the teeth recess so as to be provided curvedly along the back surface of the teeth, that is, the lingual side surface of the upper teeth. Additionally, the cover outer wall 112 forms another wall (front wall) of the teeth recess so as to be provided curvedly along the front surface (labial side surface and buccal side surface) of the teeth.

Next, the cover base 113 links the cover inner wall 111 to the cover outer wall 112 so as to cut off a gap between the teeth (upper teeth) and the opposing teeth (lower teeth). The detachable dental appliance 100 according to the present embodiment is a structure attached to the upper teeth, as mentioned above. Thus, the cover base 113 forms a bottom of the teeth recess, and the outer side surface (outer surface) of the cover base 113 contacts the lower teeth (opposing teeth) in case of clenching the lower teeth and upper teeth with the detachable dental appliance attached to the upper teeth.

For reference, the teeth of normal people are greatly divided into posterior teeth (molar teeth) and anterior teeth. An end portion of the teeth T1 (posterior teeth) constituting the posterior teeth is referred to as an occlusal surface performing a masticatory action (chewing action), and an end portion of the teeth T2 (anterior teeth) constituting the anterior teeth performs a cutting action in function, and thus is referred to as a incisal surface (or, briefly, as 'incisal edge').

Also, for normal people, the posterior teeth consists of two or three molar teeth at left and right sides of the teeth, and two premolar teeth positioned in front of the molar teeth, and the anterior teeth consists of central incisors, lateral incisors, and canines at left and right sides of the teeth.

Furthermore, the core frame 120 is provided in the inside of the cover frame 110 to contact the teeth, that is, the core frame 120 is accommodated/fixed on the inside (teeth recess) of the cover frame 110 to be engaged with a plurality of teeth among the teeth. The core frame 120 has teeth contacting surfaces 121*a* and 121*b* shaped with impressions of end portions of the plurality of teeth among the teeth (upper teeth), and is provided in the teeth recess of the cover frame 110 in an arch shape.

Thus, the core frame 120 is fixed on the teeth recess of the cover frame to complete the teeth binding recess 110*a*, mentioned above, inside the cover frame 110.

In the present embodiment, the teeth-contacting surfaces 121*a* and 121*b* of the core frame 120 are shaped with impressions of end portions of the teeth provided along the dental arch of the teeth from any one of the posterior teeth at left sides of the teeth to any one of posterior teeth at right side of the teeth.

Thus, the teeth-contacting surfaces 121*a* and 121*b* of the core frame 120 includes an anterior teeth-contacting surface 121*a* shaped with an impression of the incisal surface of the anterior teeth T2, and a posterior teeth-contacting surface 121*b* shaped with an impression of the occlusal surface of the posterior teeth T1. In a portion (a portion covering the anterior teeth) formed with the anterior teeth-contacting surface 121*a*, the teeth (central incisors, lateral incisors, and canines) constituting the anterior teeth are engaged. In a portion (a portion covering at least one posterior teeth) formed with the posterior teeth-contacting surface 121*b*, part of the teeth constituting the posterior teeth is matched.

Thus, the core frame 120 is a base for alignment and engagement when the detachable dental appliance 110 is attached to the teeth (upper teeth), and prevents the detachable dental appliance 100 from moving from an attaching location during clenching or bruxism.

In this case, an end at left side and an end at right side of the core frame 120 contact fourth posterior teeth (first premolar teeth) to sixth posterior teeth (first molar teeth) at left and right sides of the upper teeth, and the occlusal surface of the rest of the posterior teeth may contact the cover frame 110, especially, the inner side surface of the cover base 113, but is not limited thereto. The entire occlusal surfaces of the posterior teeth at left and right sides of the teeth may be covered by the core frame.

As stated above, some of the occlusal surfaces among the posterior teeth may directly contact the inner side surface (bottom surface of the teeth recess) of the cover base 113. For this, a portion occluded by contacting at least one posterior tooth among the posterior teeth may be formed in the cover base 113 of the cover frame.

More specifically, a left posterior teeth-contacting surface 102*a* occluded by directly contacting at least one of the posterior teeth at left side is formed in a gap between the end at left side of the teeth recess and the end at left side of the core frame 120 among the inner side surfaces of the cover base 113, and a right posterior teeth-contacting surface 102*b* occluded by directly contacting at least one of the posterior teeth at right side is formed in a gap between the end at right side of the teeth recess and the end at right side of the core frame 120.

The left posterior teeth-contacting surface 102*a* is shaped with an impression of at least one end portion (occlusal surface) among the posterior teeth at left side, and the right posterior teeth-contacting surface 102*b* is shaped with an impression of at least one end portion among the posterior teeth at right side.

In the present embodiment, the core frame 120 is engaged with the sixth posterior tooth at left side (first molar tooth at left side) to the sixth posterior tooth at right side (first molar tooth at right side) along the dental arch, and the seventh posterior tooth at left side (second molar tooth at left side) and the seventh posterior tooth at right side (second molar teeth at right side) are engaged with the left posterior teeth-contacting surface 102*a* and the right posterior teeth-contacting surface 102*b* formed in the left and right inner side surfaces of the cover base.

It is preferable that a thickness of the bottom (a portion covering an end portion of the teeth) at the end at left side and the end at right side of the teeth binding recess 110*a* is thinner than a thickness of a middle portion of the teeth binding recess covering the incisal surface of the anterior teeth.

The dental appliance 100 rotates with respect to the temporomandibular joint when clenching the teeth while being attached to the teeth (upper teeth), and the farthest posterior tooth (seventh or eighth posterior tooth) of the opposing teeth (lower teeth) contacts the base surface at left and right sides of the detachable dental appliance 100 first of all. Thus, when making the bottom thickness of the teeth binding recess 110*a* to be uniform, a gap between the anterior teeth of the opposing teeth and the middle portion of the detachable dental appliance may be formed, since this may cause the change in vertical position of the lower teeth and/or upper teeth.

Thus, it is preferable that the detachable dental appliance may contact at least one of the anterior teeth of the opposing teeth, at least one of the posterior teeth at left side, and at least one of the posterior teeth at right side. For this, in the detachable dental appliance, especially, in the bottom of the engagement recess of the teeth, a thickness of an anterior teeth cover part covering the end portion (incisal edge) of the maxillary anterior teeth is thicker than a thickness of a posterior teeth cover part covering an end portion (occlusal surface) of the farthest posterior tooth of the maxillary posterior teeth.

In the present embodiment, the core frame 120 is extended to the left and right sides from the fourth posterior tooth (first premolar tooth) to the sixth posterior tooth (first molar tooth) at left and right sides of the anterior teeth of the teeth (upper teeth). Thus, the posterior teeth cover part may only consist of the cover base 113, and the anterior teeth cover part may consist of the core frame 120 and the cover base 113. Thus, the posterior teeth cover part may be thinner than the anterior teeth cover part.

Of course, in case of a user with an anterior open bite, the anterior open bite may be improved by setting a thickness of the detachable dental appliance so that the detachable dental appliance contacts the posterior teeth of the opposing teeth but does not contact the anterior teeth.

Meanwhile, the second cover layer 102 is a buffer layer made of a soft material, that is, a weak material mitigating the shock applied to the teeth, that is, to the upper teeth and lower teeth, during grinding or clenching, etc., and the first cover layer 101 is a layer made of a hard material provided on the outside of the second cover layer 102, that is, a surface protective layer made of a hard material.

In the present embodiment, the first cover layer 101 forms an outer surface of the cover base 113, that is, an outer surface of the detachable dental appliance 100. Thus, when clenching the teeth with the detachable dental appliance 100 worn, the opposing teeth (the upper teeth in the present embodiment) of the teeth to which the detachable dental appliance is attached contact the first cover layer 101.

As stated in the present embodiment, it is obvious to a skilled person in the art in the related technical field that the opposing teeth may be the lower teeth when the detachable dental appliance 100 is attached to the upper teeth, and the opposing teeth may be the upper teeth when the detachable dental appliance 100 is attached to the lower teeth.

Furthermore, as the first cover layer 101 is laminated while being adjacent to the outside of the second cover layer 102, the second cover layer 102 is covered by the first cover layer 101. However, another layer may be further provided between the first cover layer 101 and the second cover layer 102. Meanwhile, as the number of layers of the cover frame 110 increases, the thickness of the detachable dental appliance increases, and accordingly, the feeling of irritation would be increased.

In the present embodiment, the second cover layer 102 is laminated on the inside of the first cover layer 101 to contact the first cover layer 101, and the inner side surface of the second cover layer 102 contacts the core frame 120 so that the core frame 120 is covered by the second cover layer 102.

Additionally, the cover inner wall 111 and the cover outer wall 112 contact the lingual side surface of the upper teeth and the front surface (buccal side and labial side) of the teeth. In the present embodiment, the cover inner wall 111, the cover outer wall 112 and the cover base 113 are integral laminar structures with the first cover layer 101 and the second cover layer 102. The second cover layer 102 contacts the lingual side surface (back surface) and front surface of the upper teeth and core frame 120. Thus, the thickness of both side walls (front wall and back wall) of the detachable dental appliance according to the present embodiment gets smaller, and the feeling of irritation may be reduced.

The core frame 120 of a firm material, that is, a hard material, may be the standard for alignment when the detachable dental appliance 100 is attached to the upper teeth, and at the same time, may maintain basic rigidity inside the detachable dental appliance 100. The first cover layer 101 maintains rigidity of the detachable dental appliance 100 along with the core frame while protecting the surface of the detachable dental appliance from the shock applied to the detachable dental appliance. Additionally, the second cover layer 102 is made of a material performing a cushioning action, that is, a buffering action, that is, a soft material. The core frame 120 and the first cover layer 101 may be made of a hard dental resin material, and the second cover layer 102 may be made of a soft dental resin material.

In the present embodiment, the first cover layer 101 may be produced with a hard resin, for example, a hard silicone resin material, and since the second cover layer 102 is a layer made of a soft material, i.e., a cushion material, that is a soft layer, it is produced with a soft silicone resin material. As dental resins, there are various hard resins and soft resins sold by companies such as EROKDENT or FORESTA-DENT in Germany. As a specific example of the hard dental resin, there is polyethylene terephthalate glycol (PETG), etc., and as a specific example of the soft dental resin, ethylene vinyl acetate (EVA) or thermoplastic polyurethane (PTU), etc. may be used. As stated above, since various hard resins with firm surfaces and soft resins with a cushioning property are known, additional explanation thereon is omitted.

The core frame 120 may be produced with a hard dental resin, but is not limited thereto. In the present embodiment, the core frame 120 is made of a hard material by mixing methyl methacrylate with polymethyl methacrylate, but is not limited thereto. Additionally, the core frame 120 may be produced with the same material as the first cover layer 101.

Meanwhile, the cover inner wall 111 and the cover outer wall 112 are elastically adhered to the back surface (lingual side surface) and front surface of the teeth to maintain the attaching state of the detachable dental appliance 100. Additionally, as stated above, the cover inner wall 111 and the cover outer wall 112 are laminar structures having a hard first cover layer 101 and a soft second cover layer 102, respectively.

A portion covering the posterior teeth among the cover inner wall 111 and the cover outer wall 112 is elastically adhered to a surface of the posterior teeth, especially, a surface of a bulge to maintain the attaching state of the detachable dental appliance 100.

According to the present invention, the second cover layer 102 reduces excessive fitting force of the detachable dental appliance 100 to prevent damage to the surface of the teeth when detaching the detachable dental appliance and induce soft wearing and wearing comfort. Additionally, the first cover layer 101 prevents damage to the surface of the detachable dental appliance 100 while maintaining rigidity and durability of the cover inner wall 111 and the cover outer wall 112, and delays the loosening of the cover frame 110 due to a long period of use.

In other words, the detachable dental appliance 100 according to the present invention includes an inner buffer layer (second cover layer) with a cushioning property and a surface protective layer (first cover layer) made of a hard material for protecting the surface. The first cover layer 101 prevents the detachable dental appliance 100 from being damaged, for example, being torn out, and at the same time, maintains a framework and rigidity of the cover frame 110. Additionally, the core frame 120 is engaged with the end of the teeth to minimize or prevent the movement of the detachable dental appliance 100 during grinding or clenching.

Thus, according to the present embodiment, the detachable dental appliance has a laminar structure of hard material-soft material-hard material. Especially, the front surface and back surface of the teeth are covered by a two-layered laminar structure of soft material-hard material. Thus, compared to the detachable dental appliance consisting of the hard material or soft material only, the detachable dental appliance of the present invention may satisfy the effects of protecting the teeth, improving detachment, fitting force (attaching force) and durability, reducing the feeling of irritation, and performing shape stability for long time use.

Referring to FIGS. 8 to 10, the detachable dental appliance 100 according to the present invention may further include engagement recesses of the opposing teeth 113a and 113b (hereinafter, 'engagement recesses') formed in a portion forming the outer surface of the cover base 113, that is, the outer side surface of the cover base among the outer side surfaces of the first cover layer 101.

In other words, the outer surface of the cover base 113 has engagement recesses 113a and 113b shaped with impressions of the opposing teeth (the lower teeth in the present embodiment) of the teeth.

More specifically, the engagement recesses 113a and 113b shaped with an impression of at least a part of the lower teeth are formed in the outer surface of the cover base 113. Since the engagement recesses 113a and 113b are formed on a position where the lower teeth are occluded, the detachable dental appliance 100 maintains the occlusion relation between the lower teeth and the upper teeth while being attached to the teeth, and also prevents the disorder of temporomandibular joint by limiting the left and right movement of the lower teeth for the upper teeth while a user holds the detachable dental appliance 100 in his mouth.

The engagement recesses include an interior teeth engagement recess 113a shaped with an impression of at least a part of the incisal surface of the anterior teeth, and a posterior teeth engagement recess 113b shaped with impressions of at least a part of the occlusal surface of the posterior teeth at left side and at least a part of the occlusal surface of the posterior teeth at right side. Thus, the detachable dental appliance 100 contacts the opposing teeth, that is, the lower teeth in at least three points.

In the present embodiment, the posterior teeth engagement recess 113b is shaped with a shallow impression of a part of the occlusal surface, especially, a part of the cusps, rather than being shaped with a deep impression of a whole of at least one posterior teeth occlusal surface. Additionally, the anterior teeth engagement recess 113a is also shaped with a shallow impression of a part of the incisal surface of the anterior teeth. The anterior teeth engagement recess and the posterior teeth engagement recess are sufficient if they prevent the lower teeth for the upper teeth from being dislocated to the left side or right side when wearing the detachable dental appliance and clenching teeth.

Meanwhile, for smooth respiration during clenching, the detachable dental appliance 100 according to the present invention further includes an airway groove 113c formed on the outer surface of the cover base 113 and allowing the outer air to pass therethrough into the mouth.

The airway groove 131 is formed in the outer surface of the cover base 113, that is, the outer side surface of the first cover layer 101. More specifically, the airway groove 131 is formed in the direction crossing the longitudinal direction of the cover frame 110, that is, in the labiolingual direction (direction from lip to tongue) at a portion covering the anterior teeth, and it is formed in the buccolingual direction at a portion covering the posterior teeth, thereby forming a respiration passage.

Additionally, the airway groove 131 is positioned in an interdental region (between the teeth) among the outer surfaces of the cover frame, and has a shape (a shape dented to the top in the present embodiment) dented to interdental direction in the interdental region among the outer surfaces of the cover base 113. In this case, the airway groove 131 is formed in a gap between the teeth (adjacent surface of the gap between the teeth) covered by the detachable dental appliance 100. Thus, it is preferable that the detachable dental appliance 100 includes a plurality of airway grooves.

Hereinafter, one embodiment of a method for producing a detachable dental appliance according to the present invention will be explained with reference to FIGS. 11 to 18.

Here, FIG. 11 is a flow chart exemplifying a method for producing the detachable dental appliance according to the present invention, FIGS. 12 and 13 are a side view and a perspective view exemplifying a state where maxillary and mandibular dental casts are supported in a joint linkage device with an occlusion relation being aligned, FIGS. 14 and 15 are a side view and a perspective view exemplifying a state where the maxillary and mandibular dental casts are widened by a joint linkage device with the occlusion relation being aligned, FIG. 16 is a perspective view illustrating a state where a core frame is molded in the dental cast, FIG. 17 is a perspective view illustrating a state where a laminar structure for a cover frame is covered on the core frame arranged in the dental cast, and FIG. 18 is a plan view illustrating a state where an engagement recess is formed on a surface of the laminar structure molded in FIG. 17.

The method for producing the detachable dental appliance 100 includes the steps of molding a core frame 120 and forming a cover frame 110.

More specifically, in the method for producing the detachable dental appliance according to the present embodiment, the core frame 120 is produced in the dental cast. For this, the dental cast of the user, for example, a mouth plaster cast is prepared. The dental cast is generally produced using impression materials and plaster. Since the method for producing the dental cast is generally known in the related field, additional explanation thereon is omitted.

The dental cast has the same structure as the teeth on which the detachable dental appliance 100 is installed. Hereinafter, the dental cast molding a structure of the teeth to which the detachable dental appliance is attached is referred to as a first dental cast M1, and the dental cast molding a structure of the opposing teeth is referred to as a second dental cast M2.

In order to produce the core frame 120 in the dental cast, especially in the first dental cast M1, as illustrated in FIGS. 13 and 14, the dental cast, more specifically, the first dental cast M1 is arranged in a base plate P of a joint linkage device. Additionally, the first dental cast M1 and the second dental cast are aligned on the base plate P so that the occlusion relation between them may be the same as the occlusion relation between the upper teeth-lower teeth of the user as much as possible.

In order to align the occlusion relation between the first dental cast M1 and the second dental cast M2, a bite with an impression of a teeth mark of the lower teeth and upper teeth of the user is mainly used.

Additionally, with the occlusion relation between the first dental cast M1 and the second dental cast M2 aligned, when the second dental cast M2 is fixed on a link bar L rotatably linked to the joint J of the joint linkage device, and the link bar L rotates with respect to the joint J of the link bar L after the second dental cast M2 is fixed on the link bar L, as illustrated in FIGS. 14 and 15, the second dental cast M2 is separated from the first dental cast M1 while rotating.

Next, as illustrated in FIG. 16, the core frame 120 may be produced in the first dental cast M1. Additionally, the core frame 120 is produced by going through a process of coating a dental resin, especially, a hard resin, on the first dental cast M2, especially, a teeth portion of the first dental cast and curing it. Of course, the core frame 120 may be produced by impressing a hard sheet, which will be mentioned later, on the first dental cast M1.

In the present embodiment, by coating the dental resin, more specifically, methyl methacrylate and polymethyl methacrylate, on the teeth portion of the first dental cast M1, the core frame 120 is molded to have the teeth-contacting surfaces 121a and 131b.

Additionally, the core frame 120 may go through a process of completing the appearance of the core frame 120 after being separated from the first dental cast M1, for example, trimming the surface of the core frame.

As stated above, after the production of the core frame 120 is completed, the step of producing the cover frame 110 is processed. For the production of the cover frame 110, with the core frame 120 arranged in the first dental cast M1, a structure with a laminar structure, that is, a laminar structure S for the cover frame 110 is molded on the outside of the core frame 120.

When explaining an example of molding the laminar structure S, the laminar structure S is formed by sequentially laminating a soft layer and a hard layer on the outside of the core frame 120, or the laminar structure S may be formed by laminating the soft layer and hard layer which are integrated with each other in a structure.

More specifically, the laminar structure S is integrally provided with the hard layer forming the first cover layer, and may be molded by the sheet including the soft layer forming the second cover layer.

For this, after softening the sheer, more particularly multi-layered sheet (for example, model name TRACK B of FORESTADENT in Germany) including the hard layer and soft layer laminated on the hard layer and integrated with the hard layer, in order for the shape of the first dental cast M1 where the core frame 120 is arranged to be transcribed in intaglio, the multi-layered sheet is integrated with the outside of the core frame 120 by adhering the multi-layered sheet to the first dental cast M1 where the core frame 120 is arranged in an adsorption or pressurization manner. Specific examples of a material forming the hard layer include a PETG material, and examples of a material forming the soft layer include an EVA material or TPU material. However, specific materials are not limited to the above-mentioned types.

Model name TRACK B by FORESTADENT in Germany disclosed as one example of the multi-layered sheet may be softened by heat. Additionally, when impressing the multi-layered sheet on the first dental cast M1 where the core frame 120 is arranged, the above-mentioned laminar structure may be formed. The laminar structure S may be produced by using a thermocompression transcription device (for example, model name TRACK of FORESTADENT in Germany).

Additionally, as stated above, the laminar structure S may be molded by sequentially laminating the soft layer and hard layer. As a more specific example, the laminar structure may be produced by going through the steps of forming the second cover layer and the first cover layer.

The second cover layer may be formed by adhering the soft sheet to the first dental cast M1 where the core frame 120 is arranged to integrate the core frame 120 with the soft sheet, so that the shape of the first dental cast M1 where the core frame 120 is arranged may be transcribed in intaglio in the soft sheet (for example, model name TRACK E by FORESTADENT in Germany) forming the second cover layer.

Additionally, the first cover layer may be formed by adhering the hard sheet to the first dental cast M1 covered by the core frame 120 and soft sheet to integrate the hard sheet with the outside of the soft sheet so that the shape of the first dental cast covered by the core frame 120 and soft sheet may be transcribed in intaglio in the hard sheet (model name TRACK A by FORESTADENT in Germany) forming the first cover layer.

The process of molding the first cover layer and the second cover layer may be also performed by using the thermocompression transcription device (for example, model name TRACK by FORESTADENT in Germany).

As the above-mentioned multi-layered sheet, hard sheet and soft sheet are thermoplastic, they are sheets which are gently softened for the molding to be possible when applying heat, the shapes thereof are impressed as they are when pressing the sheets on the dental cast, and are hardened when cooled as the shape impressed.

Additionally, in order to form the above-mentioned opposing teeth engagement recesses 113a and 113b on the outer surface of the cover frame, when impressing the second dental cast M2 on the outer surface of the laminar structure S so as to correspond to the maxillary and mandibular occlusion relation, with the core frame 120 and the laminar structure S laminated and arranged in the first dental cast M1, the engagement recesses 113a and 113b may be formed in the outer surface of the cover base 110, and accordingly, the occlusion relation between the upper teeth and the lower teeth may be maintained.

The engagement recesses 113a and 113b are formed under a state where the laminar structure S is softened, that is, under a temperature where molding is possible. At a temperature right after the laminar structure S is molded, the engagement recesses 113a and 113b may be formed. Thus, as illustrated in FIG. 17, when rotating downwardly the link bar L (see FIGS. 12 to 15) of the joint linkage device and pressurizing the laminar structure S with the second dental cast M2 so that the second dental cast M2 may be impressed on the surface of the laminar structure S in the state where the first dental cast M1 is covered by the core frame 120 and laminar structure S, the teeth portion of the second dental cast M2, especially, the end portion of the teeth is impressed on the surface of the laminar structure S, and as illustrated in FIG. 18, the engagement recesses 113a and 113b are formed on the surface of the laminar structure S.

Next, as illustrated in FIG. 18, by going through the steps of separating the laminar structure S integrated with the core frame 120 from the first dental cast M1, cutting the laminar structure S, trimming the surface, etc. to complete the appearance of the cover frame 110 with the arch shape, the detachable dental appliance 100 with the arch-shape may be completed.

As mentioned above, the detachable dental appliance may be produced using the dental cast of the user, and may be produced by a three-dimensional molding machine by transmitting three-dimensional data of the detachable dental appliance planned (designed) on the computer using CAD/CAM and designed on the computer to the three-dimensional molding machine.

While the preferred embodiments according to the present invention have been described above, it is obvious to those skilled in the art that in addition to the aforementioned embodiments, the present invention may be implemented as other specific forms without departing from the purpose and the scope of the present invention.

Accordingly, the aforementioned embodiments should be only illustrative and not restrictive for this invention, and thus, the present invention is not limited to the aforementioned description, but may be modified within the scope of the appended claims and equivalents thereto.

MODES FOR INVENTION

Another embodiment of the detachable dental appliance according to the present invention is explained with reference to FIGS. 19 to 22. FIG. 19 is a perspective view illustrating another embodiment of the present invention, FIG. 20 is a side view illustrating a state where the teeth protector is attached to the maxillary teeth, FIG. 21 is a cross-sectional view taken along line A-A of FIG. 19, and FIG. 22 is a cross-sectional view taken along line B-B of FIG. 19.

The teeth protector, as a specific example of the detachable dental appliance according to the present invention, is a device applicable to protect the teeth by being attached to the upper teeth or lower teeth and maintain tooth alignment, which may be used as a mouth piece, and may also be applicable as another intraoral device in the form of a mouth piece such as a retainer of teeth alignment. In the present embodiment, a structure where the detachable dental appliance, more specifically, the teeth protector is attached to the maxillary teeth (upper teeth) is explained, but it may also have a structure attached to the mandibular teeth (lower teeth).

Referring to FIGS. 19 to 22, the detachable dental appliance 200 in the present embodiment is attached to the maxillary teeth (upper teeth) to protect the teeth of the user. As mentioned above, the detachable dental appliance may be used as an apparatus for preventing damage to the teeth from grinding or clenching and other shock, and may also be used as an apparatus for maintaining the current tooth alignment, for example, an orthodontic retainer maintaining the tooth alignment after orthodontic treatment or a splint, other aligners, etc.

In the detachable dental appliance 200 (hereinafter, explained based on the 'teeth protector'), the teeth recess 200a into which the teeth, that is, the upper teeth are inserted is formed in intaglio with a shape corresponding to the maxillary dental arch. Additionally, the teeth protector 200 includes a guard inner wall 210, a guard outer wall 220, and a guard base 230.

Here, the guard inner wall 210 forms one side wall (inner side wall or back wall) of the teeth recess 200a so as to contact the lingual side surface of the teeth, that is, the upper teeth, and is formed along the lingual side of the upper teeth so as to cover the lingual side surface of the upper teeth.

Also, the guard outer wall 220 forms another side wall (outer side wall or front wall) of the teeth recess 200a so as to contact the outer side surface (labial side surface and buccal side surface) of the teeth, and is formed along the buccal side and labial side of the upper teeth so as to cover the outer side surface of the upper teeth.

Next, the guard base 230 covers the incisal surface of the anterior teeth forming the end portion of the teeth and the occlusal surface of the posterior teeth at left and right sides of the teeth, which cuts off the contact of the lower teeth with the upper teeth when clenching the lower teeth and upper teeth.

For reference, the teeth of normal people are greatly divided into posterior teeth and anterior teeth T2. The end of the teeth T1 (hereinafter, the same reference numeral is used in 'posterior teeth') constituting the posterior teeth is referred to as an occlusal surface performing a masticatory action (chewing action), and the end of the teeth T2 (hereinafter, the same reference numeral is used in 'anterior teeth') constituting the anterior teeth performs a cutting action in function, and thus is referred to as a incisal surface. For normal people, the posterior teeth T1 consists of two or three molar teeth at left and right sides of the teeth, and two premolar teeth positioned in front of the molar teeth, and the anterior teeth T2 consists of central incisors, lateral incisors, and canines at left and right sides of the teeth.

The teeth-contacting surfaces 201 and 202 shaped with impressions of the end portions of the teeth are provided in the inner side surface of the guard base 230, that is, in the bottom surface of the teeth recess 200a. Additionally, the teeth-contacting surfaces include an anterior teeth-contacting surface 201 shaped with an impression of the incisal surface and a posterior teeth-contacting surface 202 shaped with an impression of the occlusal surface. In a portion (a portion covering the anterior teeth) formed with anterior teeth-contacting surface 201, the teeth T2 (central incisors, lateral incisors, and canines) constituting the anterior teeth are matched, and in a portion (a portion covering the posterior teeth) formed with the posterior teeth-contacting surface, the teeth T2 (premolar teeth and molar teeth) constituting the posterior teeth are matched.

Furthermore, the guard base 230 includes a buffer layer 231, an inner base layer 232 and an outer base layer 233.

Here, the buffer layer 231 is a layer made of a soft material mitigating the shock applied to the teeth, that is, the upper teeth, during grinding, or clenching, etc. The inner base layer 232 is a layer of a hard material provided in the inside of the buffer layer 231, and the outer base layer 233 is a layer of a hard material provided in the outside of the buffer layer 231.

In the present embodiment, the inner base layer 232 contacts the end portion of the teeth, and the outer base layer 233 forms the outer surface of the guard base, that is, the surface (the base surface in case of the teeth protector attached to the maxilla, and the upper surface in case of the teeth protector attached to the mandible) contacting the opposing teeth of the teeth to which the teeth protector is attached when clenching the teeth while wearing the teeth protector. As in the present embodiment, it is obvious to a skilled person in the art that when the teeth protector is attached to the upper teeth, the opposing teeth would be the lower teeth.

Additionally, the inner base layer 232 is laminated while being adjacent to the inner side surface of the buffer layer 231, and the outer base layer 233 is laminated while being adjacent to the outer side of the buffer layer, and thereby the buffer layer 231 is covered by the outer base layer 233. However, a gap between the buffer layer 231 and the inner base layer 232 and/or a gap between the buffer layer 231 and the outer base layer 233 may be divided by at least one other layer. Meanwhile, as the number of layer of the teeth protector increases, the thickness thereof also increases, and thereby the feeling of irritation also increases.

The anterior teeth-contacting surface 201 and the posterior teeth-contacting surface 202 are formed in the surface of the inner base layer 232. The inner base layer 232 and the outer base layer 233 are made of a firm material, that is, a hard material. Additionally, the buffer layer 231 is made of a material performing a cushioning action, i.e., a buffering action, that is, a soft material. The inner base layer 232 and the outer base layer 233 may be made of a hard dental resin material, and the buffer layer 231 may be made of a soft dental resin material.

Since the inner base layer 232 has the teeth-contacting surfaces 201 and 202, it becomes the standard for alignment when the teeth protector is attached to the upper teeth, and at the same time, maintains rigidity of the guard base. Additionally, the outer base layer 233 maintains rigidity of the guard base 230 along with the inner base layer 232 while protecting the guard base 230 from external shock.

In the present embodiment, the inner base layer 232 and the outer base layer 233 may be produced with a hard resin, for example, a hard silicone resin, and since the buffer layer 231 is a layer made of a soft material, i.e., a cushion material, that is a soft layer, it may be produced with a soft silicone resin. As dental resins, there are various hard resins and soft resins sold by various companies such as EROKDENT or FORESTADENT in Germany. As a specific example of the hard dental resin, there is polyethylene terephthalate glycol (PETG), etc., and as a specific example of the soft dental resin, ethylene vinyl acetate (EVA) or thermoplastic polyurethane (PTU), etc. may be used. As stated above, since various hard resins with firm surfaces and soft resins with a cushioning property are known, additional explanation thereon is omitted.

Meanwhile, referring to FIGS. 23 to 27, the guard base 230 may be configured to contact the posterior teeth T3 and anterior teeth T4 of the opposing teeth (the lower teeth in the present embodiment). For this, the portion covering the anterior teeth T2 of the teeth (upper teeth) in the guard base is formed to be thicker than the portion covering the posterior teeth T1 at both sides of the teeth.

More specifically, it is preferable that the guard base 230 further includes a thickness supplementing part which supplements a thickness of the portion covering the anterior teeth T2.

This is because when clenching the teeth while the teeth protector 200 is attached to the upper teeth, the teeth T4 (especially, the anterior teeth of the lower teeth) which do not contact the teeth protector 200 may change their vertical positions, and thereby the teeth alignment may be collapsed.

In the present embodiment, the thickness supplementing part 234 is provided on the inside of the outer base layer 233. More specifically, the thickness supplementing part 234 is formed in the outer side of the inner base layer 232 so as to be provided on the inside of the buffer layer 231 so that it may be covered by the buffer layer 231.

The thickness supplementing part 234 is made of a hard material, that is, a firm material, but is not limited thereto. In the present embodiment, the thickness supplementing part 234 is formed by coating methyl methacrylate and polymethyl methacrylate on the outer surface of the inner base layer 232, that is, the portion covering the anterior teeth T2, and curing it, but the materials thereof are not limited thereto.

Meanwhile, the guard inner wall 210 and guard outer wall 220 are elastically adhered to the lingual side surface and outer side surface of the teeth, thereby maintaining the attaching state of the teeth protector 200. Additionally, the guard inner wall 210 and guard outer wall 220 include soft first side surface layers 211 and 221, and hard second side surface layers 212 and 222 provided on one side of the first side surface layers 211 and 221.

According to the present invention, the first side surface layers 211 and 221 reduce excessive fitting force of the teeth protector 200 to prevent damage to the surface of the teeth when detaching the teeth protector 200 and induce easy wearing. Additionally, the second side surface layers 212 and 222 are provided on the outside of the first side surface layers 211 and 221 to prevent damage to the side of the teeth protector while maintaining rigidity of the guard inner wall 210 and the guard outer wall 220.

In other words, the teeth protector according to the present invention includes a buffer layer with a cushioning property and a hard reinforcing layer (a hard layer) made of a harder material than the buffer layer. The hard layer prevents the teeth protector from being damaged, for example, being torn out, and at the same time, maintains a framework (shape) of the posterior teeth guard. Especially, the hard inner base layer is engaged with the end of the teeth to minimize or prevent left and right movements of the teeth protector during grinding or clenching.

According to the present embodiment, the first side surface layer 211 of the guard inner wall contacts the lingual side surface of the teeth, and the first side surface layer 221 of the guard outer wall contacts the outer side surface (labial side surface and buccal side surface) to protect the surface of the teeth. Additionally, the second side surface layers 212 and 222 of the guard inner wall and the guard outer wall are laminated with a structure adjacent to the outside of the first side surface layers 211 and 221, so they cover the first side surface layers 211 and 221.

The first side surface layers 211 and 221 are integrally formed with the buffer layer 231 of the guard base 230 with the same material, and the second side surface layers 211 and 221 may be integrally formed with the outer base layer 233 of the guard base with the same material. That is, in the present embodiment, the buffer layer 231 of the guard base has a laminar structure which is extended to cover the lingual side surface and outer side surface of the teeth, thereby forming the first side surface layers 211 and 221 of the guard inner wall and the guard outer wall, and the outer base layer 233 of the guard base has a laminar structure which is extended to cover the first side surface layers 211 and 221 of the guard inner wall and the guard outer wall to form the second side surface layers 212 and 222 of the guard inner wall and the guard outer wall.

The portion covering the posterior teeth of the guard inner wall 210 and the guard outer wall 220 is elastically adhered to the surface of the posterior teeth, especially, the surface of the bulge to maintain the attaching state of the teeth protector.

Thus, according to the present embodiment, the portion covering the posterior teeth at both sides of the teeth (upper teeth) in the guard base of the teeth protector may include a laminar structure of hard material-soft material-hard material, and the portion covering the anterior teeth may include a laminar structure of hard material-soft material-hard material or a laminar structure of hard material-hard material-soft material-hard material. Additionally, as in the present embodiment, the guard inner wall 210 and the guard outer wall 220 may be formed with a two-layered laminar structure of soft material-hard material unlike the guard base. This structure may reduce the thickness in comparison with the laminar structure of at least three layers like the guard base, and may achieve the function of protecting the teeth, improving detachment, fitting force (attaching force) and reducing the feeling of irritation, etc. compared to the guard inner wall and the guard outer wall made of a hard material or soft material only.

Of course, in case of a user with an anterior open bite, the anterior open bite may be improved by setting the thickness of the guard base so that the portion covering the anterior teeth of the upper teeth in the guard base of the teeth protector does not contact the anterior teeth of the lower teeth.

Meanwhile, for smooth respiration during clenching, the teeth protector 200 according to the present invention further includes an airway groove 231 formed on the outer surface of the teeth protector 200 and guiding outdoor air (outside air) of the dental arch to the inside of the dental arch (inside the mouth).

The airway groove 231 is formed in the surface of the teeth protector 200, that is, the outer surface (the base surface in the present embodiment) of the guard base 230. More specifically, the airway groove 231 is formed in the direction crossing the dental arch, that is, in the labiolingual direction at a portion covering the anterior teeth, and it is formed in the buccolingual direction at a portion covering the posterior teeth, thereby forming a respiration passage.

Additionally, the airway groove 231 is positioned in an interdental region (between the teeth), and has a shape (a shape dented to the top in the present embodiment) dented to interdental direction in the interdental region among the outer surface of the guard base 230. In this case, the airway groove 231 is formed in a gap between the teeth (adjacent surface of the gap between the teeth) covered by the teeth protector. Thus, it is preferable that the teeth protector includes a plurality of airway grooves.

The teeth protector may be designed on the computer using CAD/CAM, and may be produced by a three-dimensional molding machine. It may be produced through a process of sequentially coating/curing the hard resin and soft resin to conform to the above-mentioned structure in the dental cast shaped with an impression of a mouth structure of the user, for example, a maxillary plaster cast.

When heating the hard sheet produced with the hard resin, for example, the sheet made of PETG material (for example, model name TRACK A by FORESTADENT in Germany) to transcribe the teeth alignment structure of the user by impressing the sheet on a teeth area shaped with the mouth, and impressing the soft sheet, for example, the sheet made of EVA material or TPU material (for example, model name TRACK E by FORESTADENT in Germany) thereon to impress the hard sheet on it again, or impressing the multi-layered sheet (for example, model name TRACK B by FORESTADENT in Germany) with a multi-layered structure of soft material and hard material, the above-mentioned laminar structure may be made. The teeth protector with the above-mentioned structure may be produced by using the thermocompression molding device (for example, model name TRACK by FORESTADENT in Germany).

Next, other embodiments of the present invention are explained with reference to FIGS. 28 to 31. FIG. 28 is a perspective view illustrating yet another embodiment of the present invention, FIG. 29 is a cross-sectional view taken along line I-I of FIG. 28 illustrating one example of the posterior teeth guard, FIG. 30 is a side view of the embodiment, and FIG. 31 is a plan view of the embodiment.

The detachable dental appliance according to the present embodiment may be applied to various intraoral devices with a mouth piece shape such as a mouth guard or splinter, orthodontic retainer or orthodontic aligner, etc. protecting the teeth. Hereinafter, a structure where the mouth guard, one example of the detachable dental appliance, is attached to the maxillary teeth is explained.

Referring to FIGS. 28 to 31, the detachable dental appliance 300 of the present embodiment performs dental functions such as protecting the teeth of the user or maintaining the tooth alignment, etc. while being attached to the maxillary teeth. The detachable dental appliance 300 (hereinafter, explanation will be made based on 'mouth guard') includes a posterior teeth guard 310 covering the posterior teeth T1 (molar) among the teeth.

As explained in the embodiment mentioned above, for normal people, the posterior teeth T1 consists of two molar teeth and two premolar teeth positioned in front of the molar teeth, and the posterior teeth guard 310 covers at least one tooth among the posterior teeth, preferably, all posterior teeth.

The posterior teeth guard 310 includes a guard base 313 and guard side walls 314 and 314b, and the guard base 313 covers the occlusal surface of the posterior teeth to cut off a gap between the posterior teeth T1 and the opposing teeth of the posterior teeth. Additionally, the guard side walls 314a and 314b cover the side surface of the posterior teeth, and are integrally formed with the guard base 313.

More specifically, the guard base 313 includes a buffer layer 313a which absorbs shock from an occlusal force between the posterior teeth and the opposing teeth (posterior teeth in the lower teeth in the present embodiment), and a hard layer 313b of a firm material provided on the inside or outside of the buffer layer 313a to reinforce the strength of the guard base 313.

That is, the guard base 313 includes a buffer layer with a cushioning property and a hard reinforcing layer (a hard layer) made of a harder material than the buffer layer. The hard layer prevents the guard base from being damaged, for example, being torn-out, and at the same time, maintains a framework (shape) of the posterior teeth guard.

According to the present embodiment, the hard layer 313b is a structure covered by the buffer layer 313a, which contacts the occlusal surface of the posterior teeth, and the hard layer 313b has the posterior teeth-contacting surface 313c with a shape where the occlusal surface of the posterior teeth is transcribed. However, the structure of the guard base 313 is not limited thereto.

For example, the positions of the buffer layer 313a and hard layer 313b may be changed, and accordingly the buffer layer may be covered by the hard layer 313b, and the posterior teeth-contacting surface may be formed in the buffer layer 313a.

Additionally, in the present embodiment, the guard base 313 consists of a one-layer buffer layer 313a and a one-layer hard layer 313b. However, at least one of the buffer layer 313a and hard layer 313b may have two layers.

For example, the guard base 313 may have a structure where the buffer layer 313a is laminated on the outer side and inner side of the hard layer 313b, or may have a structure where the hard layer 313b is laminated on the outer side and inner side of the buffer layer 313a.

Also, the guard side walls 314a and 314b include side surface layers integrally formed with the buffer layer with the same material, and the guard base 313 and guard side walls 314a and 314b form posterior teeth recess 310a with a shape where the posterior teeth is transcribed to be inserted.

Of course, the guard side walls 314a and 314b may include the side surface layers integrally formed with the hard layer 313b with the same material. However, in the present embodiment, the buffer layer 313a is extended to cover the lingual side surface and buccal side surface of the posterior teeth to form the guard side walls 314a and 314b.

More specifically, the guard side walls 314a and 314b include posterior teeth buccal side wall 314a adhered to the buccal side surface of the posterior teeth, and a posterior teeth lingual side wall 314b adhered to the lingual side surface of the posterior teeth. The guard side walls are elastically adhered to the surface of the posterior teeth, especially to the surface of the bulge to maintain the attaching state of the posterior teeth guard 310 so that the posterior teeth guard 310 may not be separated from the posterior teeth.

In this case, the posterior teeth buccal side wall 314a and the posterior teeth lingual side wall 314b include the buffer layer of the guard base 313 or the layer with the same material as the hard layer, that is, the side surface layer. In the present embodiment, the posterior teeth buccal side wall 314a and the posterior teeth lingual side wall 314b are formed of a single layer with the same material as the buffer layer 313a, but are not limited thereto.

Additionally, the posterior teeth guard 310 is a molar guard which is divided into a left guard 311 for protecting the left molar teeth (posterior teeth at left side or left posterior teeth), and a right guard 312 for protecting the right molar teeth (posterior teeth at right side or right posterior teeth). The left guard 311 and the right guard 312 are integrally linked by a connector 320.

Here, a left posterior teeth recess with a shape where the posterior teeth at left side is transcribed is formed in the left guard 311 so that the posterior teeth at left side may be inserted, and a right posterior teeth recess with a shape where the posterior teeth at right side is transcribed is formed in the right guard 312 so that the posterior teeth at right side may be inserted. That is, the posterior teeth recess formed in the left guard 311 becomes the left posterior teeth recess, and the posterior teeth recess formed in the right guard 312 becomes the right posterior teeth recess.

In the present embodiment, the connector 320 includes an anterior teeth guard to which the maxillary anterior teeth are inserted. Hereinafter, the same reference numeral as the connector 320 is applied to the anterior teeth guard.

The anterior teeth guard 320 is formed with an anterior teeth recess 320a with a shape where the anterior teeth (in the present embodiment, incisors and canines are included) is transcribed. The anterior teeth recess 320a and the posterior teeth recess 310a, that is, the left posterior teeth recess and right posterior teeth recess are formed with the same arrangement structure as the maxillary dental arch, that is, the arrangement structure following the dental arch.

The anterior teeth guard 320 includes an anterior teeth lingual side wall 321 positioned at the lingual side of the anterior teeth, and an anterior teeth labial side wall 322 positioned at the labial side of the anterior teeth. The anterior teeth recess 320a is formed between the anterior teeth lingual side surface wall 321 and the anterior teeth labial side wall 322, and the incisal surface of the anterior teeth is covered by a bottom portion of the anterior teeth recess 320a.

Meanwhile, for smooth respiration during clenching, the mouth guard 300 according to the present invention further includes an airway groove 311 formed on the outer surface of the mouth guard 300 and guiding the outdoor air (outside air) of the dental arch to the inside of dental arch.

The airway groove 331 is formed in the bottom surface (the base surface in the present embodiment) of the mouth guard 300. More specifically, the airway groove is formed in the direction crossing the dental arch, that is, in the buccolingual direction in the posterior teeth guard 310, and in the labiolingual direction in the anterior teeth guard 320.

Additionally, the airway groove 331 is positioned in an interdental region (between the teeth), and has a shape (a shape dented to the top in the present embodiment) dented to interdental direction in the interdental region among the bottom surface of the mouth guard 300.

Thus, the posterior teeth guard 310 is formed on the outer surface (bottom surface) of the guard base 313, and the anterior teeth guard 320 is formed on the bottom surface of the bottom portion covering the anterior teeth. In this case, it is preferable that the airway groove 331 is formed in a gap between the teeth (adjacent surface of the gap between the teeth), and it is preferable that the mouth guard includes a plurality of airway grooves.

Additionally, the anterior teeth guard 320 may include a guard frame 321a provided along at least one side of the lingual side and labial side of the anterior teeth so that the mouth guard 300 maintains the shape of the dental arch.

Referring to FIG. 31, in the present embodiment, the guard frame 321a is made of a firm material provided in the anterior teeth lingual side wall 321, and maintains the shape of the mouth guard 300 to its original state. In the present embodiment, the guard frame 321a is made of the same material as the hard layer 313b, and is integrally connected to the hard layer 313b, but is not limited thereto.

Also, in the present embodiment, the hard layer 313b may be produced with hard resin, for example, a hard silicone resin material, and since the buffer layer 313a is a layer made of a soft material, that is a soft layer, it is produced with a soft silicone resin material. As dental resins, there are various hard resins and soft resins sold by companies such as EROKDENT, etc. in Germany. As a specific example of the hard dental resin, there is polyethylene terephthalate glycol (PETG), etc., and as a specific example of the soft dental resin, there is ethylene vinyl acetate (EVA), etc. As stated above, since various hard resins and soft resins are known, additional explanation thereon is omitted.

Next, other embodiments of the posterior teeth guard of the mouth guard, which is one example of the detachable dental appliance, is explained with reference to FIGS. 32 to 37.

As described in the examples illustrated in FIGS. 32 and 33, the posterior teeth guard 310 may have a structure where the hard layer 313b is buried inside the buffer layer 313a. The hard layer may be a hard resin, and may be a metal thin-film, especially, a porous metal mesh plate. As an example of the metal mesh plate, products by TOMY in Japan may be applied.

Furthermore, as illustrated in FIG. 34, the guard side walls 314a and 314b are integrally formed with the buffer layer 313a as a single layer with the same material, and the buffer layer 313a may be covered by the hard layer 313b. Of course, the guard side walls 314a and 314b may be integrally formed with the hard layer 313b as a single layer with the same material, and the hard layer 313b may be covered by the buffer layer 313a.

Additionally, as illustrated in FIG. 35, the guard side walls 314a and 314b and guard base 313 may have a structure with at least three layers. For example, the guard side walls may have a laminar structure where the buffer layer 313a is provided between the hard layers 313b, or the hard layer 313b is provided between the buffer layers 313a.

Next, referring to FIGS. 36 and 37, the opposing teeth-contacting surface 113d with a shape where the occlusal surface of the opposing teeth is transcribed may be formed on the opposing surface of the posterior teeth-contacting surface, that is, the outer surface of the guard base, and thus the occlusion relation between the lower teeth and upper teeth may be maintained to its original state. Additionally, as illustrated in FIG. 37, the posterior teeth guard 310 may further include the opposing teeth buccal side wall 314c contacting the buccal side surface of the opposing teeth, and the opposing teeth lingual side wall 314d contacting the lingual side surface of the opposing teeth.

Meanwhile, the detachable dental appliance according to the present invention, for example, the mouth guard may further include a handle for detaching the mouth guard.

Referring to FIGS. 38 and 39, the mouth guard 300A in another embodiment includes the posterior teeth guard 310 and the anterior teeth guard 320. The handle for detachment 330 is provided in the anterior teeth guard 320, from which the detachable dental appliance, that is the mouth guard may be easily removed to the outside of the mouth by the user and other people.

In the present embodiment, the handle 330 is fixed on a front surface of the anterior teeth guard 320, that is, a front surface of the anterior teeth labial side wall 322. More specifically, the handle is provided to be bent downwardly to the front surface (front surface of the anterior teeth labial side wall) of the anterior teeth guard 320.

The handle 330 may be provided in the state folded by itself on the front surface of the anterior teeth guard 320, and may be folded by external force pressing the lip. In the present embodiment, the end of the handle 330 is fixed on the top of the front surface of the anterior teeth labial side wall 322 and is folded downwardly by its elasticity.

More specifically, the handle 330 has a ring structure where both ends thereof are fixed on the top of the front surface of the anterior teeth labial side wall 322, which may minimize the feeling of irritation applied to the lip by the handle 330 mounted with the mouth guard 300A according to the present embodiment inside the mouth.

Also, when detachment of the mouth guard 300A is required, the mouth guard 300A, that is, the detachable dental appliance, may be easily separated from the teeth by allowing the user or other people to hold the handle 300 using their finger or other tools, bending back the handle from a position of a dotted line to a position of a full line, and pulling the handle in the direction of an arrow in FIG. 39.

The handle 330 for detaching the guard may be operated being held by the hand, especially, the finger, and may be operated by other machines or tools. Thus, the handle is not limited to a feature directly held by the hand.

For the rest of the features except for the handle 330 for detaching guard, the structure explained in the embodiments above may be applied, so redundant explanation will be omitted.

While the preferred embodiments according to the present invention have been described above, it is obvious to those skilled in the art that in addition to the aforementioned embodiments, the present invention may be implemented as other specific forms without departing from the purpose and the scope of the present invention.

Accordingly, the aforementioned embodiments should be only illustrative and not restrictive for this invention, and thus, the present invention is not limited to the aforementioned description, but may be modified within the scope of the appended claims and equivalents thereto.

INDUSTRIAL AVAILABILITY

The present invention relates to an intraoral device, that is, a detachable dental appliance with the shape of a mouth piece to be detachably attached to the teeth, which is industrially applicable in the fields of producing apparatuses for orthodontic treatment or mouth guards for sports, etc. Additionally, the detachable dental appliance absorbs shock due to clenching or grinding to prevent damage to teeth, is effective in maintaining tooth alignment, and is outstandingly durable in sustained use.

What is claimed is:

1. A dental appliance with an arch shape detachably attached to upper teeth or lower teeth forming a dental arch, comprising:
a cover frame formed with a teeth recess extending in a longitudinal direction of the cover frame, the cover frame being a laminar structure including a first cover layer of a hard material and a second cover layer of a soft material provided at an inside relative to the first cover layer; and
a core frame of a hard material provided in the teeth recess of the cover frame and having a teeth-contacting surface shaped with impressions of end portions of teeth to which the dental appliance is attached,
wherein the cover frame includes a cover inner wall forming a wall on one side of the teeth recess so as to be provided on a lingual side of the teeth, a cover outer wall forming a wall on other side of the teeth recess so as to be provided on a front side of the teeth, and a cover base connecting the cover inner wall and the cover outer wall so as to cover the end portions of the teeth,
wherein the cover inner wall directly contacts lingual surfaces of the teeth, and the cover outer wall directly contacts front surfaces of the teeth,
wherein a left posterior teeth-contacting surface is shaped with impressions of end portions of at least one of posterior teeth at a left side of the dental arch and is formed on an inner surface of the cover base of the cover frame so as to directly contact the at least one of the posterior teeth at the left side to be occluded, and a right posterior teeth-contacting surface is shaped with impressions of end portions of at least one of posterior teeth at a right side of the dental arch and is formed on the inner surface of the cover base of the cover frame so as to directly contact the at least one of the posterior teeth at the right side to be occluded, and
wherein the left posterior teeth-contacting surface is disposed between a left side end of the cover frame and a left side end of the core frame, and the right posterior teeth-contacting surface is disposed between a right side end of the cover frame and a right side end of the core frame.

2. The dental appliance according to claim 1, wherein the teeth-contacting surface of the core frame is shaped with impressions of end portions of the teeth from any one of posterior teeth at a left side of the dental arch to any one of posterior teeth at a right side of the dental arch.

3. The dental appliance according to claim 1, wherein a thickness of an anterior teeth cover part covering end portions of anterior teeth of the teeth is thicker than a thickness of a posterior teeth cover part covering end portions of farthest posterior teeth among posterior teeth of the teeth.

4. The dental appliance according to claim 1, wherein the first cover layer forms an outer surface of the detachable dental appliance, the second cover layer is laminated on an inner surface of the first cover layer to contact the first cover layer, and the core frame is disposed on an inner surface of the second cover layer, and
wherein the second cover layer of the cover frame directly contacts the lingual surfaces and the front surfaces of the teeth, while the core frame directly contacts only the end portions of the teeth.

5. The dental appliance according to claim 1, wherein the second cover layer has an inside surface directly contacting the lingual surfaces of the teeth, the front surfaces of the teeth, and the core frame.

6. The detachable dental appliance according to claim 1, wherein an outer surface of the cover base is shaped with impressions of opposing teeth occluded by the teeth.

7. The detachable dental appliance according to claim 1, wherein the cover base has at least one airway groove dented on an interdental portion of an outer surface of the cover base, the airway groove extending perpendicular to the longitudinal direction of the cover frame to allow air to pass through to a back of the cover frame.

8. The detachable dental appliance according to claim 1, wherein the second cover layer of the cover frame directly contacts the lingual surfaces and the front surfaces of the teeth, while the core frame directly contacts only the end portions of the teeth.

9. The detachable dental appliance according to claim 1, wherein the left posterior teeth-contacting surface is disposed to contact a posterior tooth located at a left end of the dental arch, and the right posterior teeth-contacting surface is disposed to contact a posterior tooth located at a right end of the dental arch.

10. The dental appliance according to claim 1, wherein the left and right posterior teeth-contacting surfaces are formed on portions of the second cover layer located at the cover base, respectively.

\* \* \* \* \*